US012391004B2

(12) United States Patent
McAlpine et al.

(10) Patent No.: US 12,391,004 B2
(45) Date of Patent: Aug. 19, 2025

(54) THREE DIMENSIONAL PLACEMENT OF ORGANISMS

(71) Applicant: Regents of the University of Minnesota, Minneapolis, MN (US)

(72) Inventors: Michael C. McAlpine, Minneapolis, MN (US); Guebum Han, Minneapolis, MN (US); John C. Bischof, Saint Paul, MN (US); Kanav Khosla, St Paul, MN (US); Kieran T. Smith, Minneapolis, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 17/813,779

(22) Filed: Jul. 20, 2022

(65) Prior Publication Data

US 2023/0025400 A1    Jan. 26, 2023

Related U.S. Application Data

(60) Provisional application No. 63/223,908, filed on Jul. 20, 2021.

(51) Int. Cl.
*B29C 64/393* (2017.01)
*B01L 3/00* (2006.01)
(Continued)

(52) U.S. Cl.
CPC ............ *B29C 64/393* (2017.08); *B01L 99/00* (2013.01); *B29C 64/209* (2017.08); *B33Y 10/00* (2014.12); *B33Y 30/00* (2014.12); *B33Y 50/02* (2014.12); *C12N 5/0062* (2013.01); *B01L 2200/06* (2013.01); *B01L 2400/02* (2013.01); *B01L 2400/049* (2013.01)

(58) Field of Classification Search
None
See application file for complete search history.

(56) References Cited

U.S. PATENT DOCUMENTS

| 2012/0028240 A1* | 2/2012 | Richmond | ............ C12M 33/06 |
| | | | 435/3 |
| 2012/0252115 A1* | 10/2012 | Suh | ...................... C12N 15/101 |
| | | | 435/320.1 |

OTHER PUBLICATIONS

Khosla et al., "Cryopreservation and Laser Nanowarming of Zebrafish Embryos Followed by Hatching and Spawning," Advanced Biosystems, Sep. 2020, 11 pp.

(Continued)

*Primary Examiner* — Brian R Gordon
(74) *Attorney, Agent, or Firm* — Shumaker & Sieffert, P.A.

(57) ABSTRACT

A system includes a placement head with at least one printing nozzle configured to pick up and detachably hold at least one biological organism; an image acquisition system including a visual inspection system configured to identify at least one target biological organism to be picked up by the printing nozzle of the placement head in a first location, and identify at least one second location for deposit of the at least one target biological organism, wherein the first location is different from the at least one second location; and a robotic motion system that moves the placement head, based on input from the visual inspection system and a distance identification system, from the first location to the at least one second location, such that the placement head deposits the target biological organism at the at least one second location.

18 Claims, 25 Drawing Sheets

(51) Int. Cl.
   *B01L 99/00*    (2010.01)
   *B29C 64/209*   (2017.01)
   *B33Y 10/00*    (2015.01)
   *B33Y 30/00*    (2015.01)
   *B33Y 50/02*    (2015.01)
   *C12N 5/00*     (2006.01)

(56) References Cited

OTHER PUBLICATIONS

Khosla et al., "Gold Nanorod Induced Warming of Embryos from the Cryogenic State Enhances Viability," ACS Nano, Jul. 2017, 10 pp.
Zhan et al., "Cryopreservation Method for *Drosophila* Melanogasler Embryos," Nature Communications, vol. 12, Apr. 3, 2021, 10 pp.
Zhang et al., "Robotic Pick-and-Place of Multiple Embryos for Vitrification," IEEE Robotics and Automation Letters, vol. 2, No. 2, Apr. 2017, pp. 570-576.

* cited by examiner

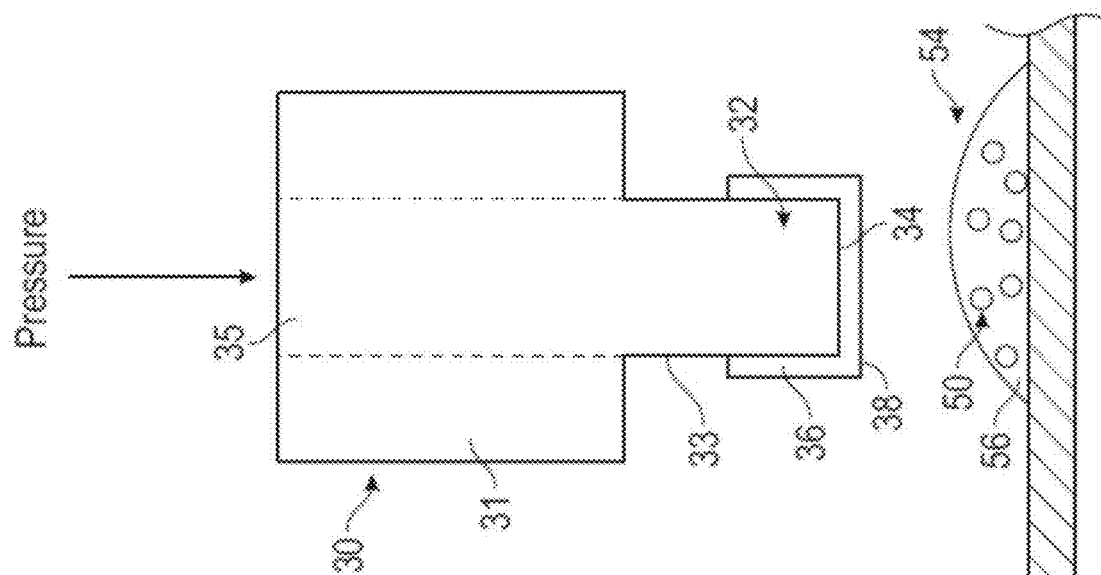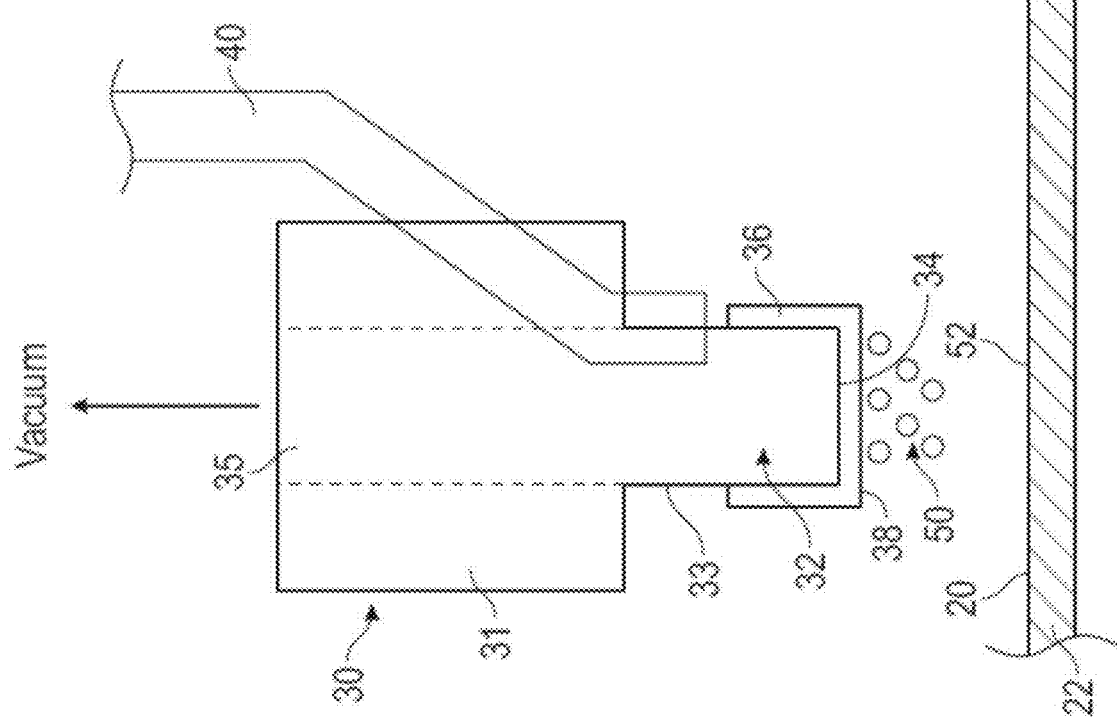
FIG. 2

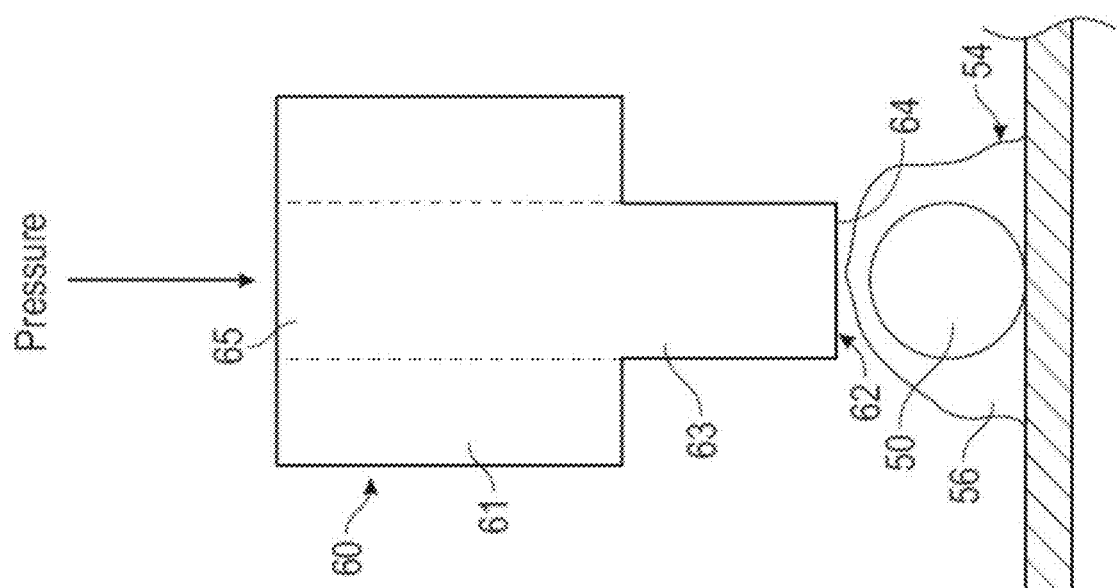
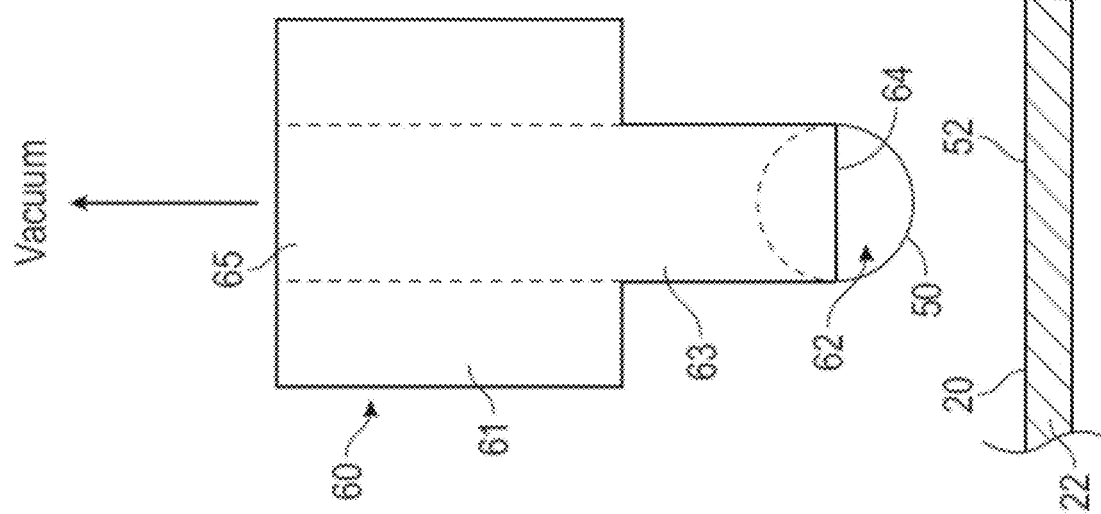
FIG. 3

```
                                                          ┌─ 202
                                                         ▼

┌─────────────────────────────────────────────────────┐
│ IDENTIFY TARGET BIOLOGICAL ORGANISM AT A FIRST      │─── 202
│ LOCATION ON A SUBSTRATE                             │
└─────────────────────────────────────────────────────┘
                          │
                          ▼
┌─────────────────────────────────────────────────────┐
│ APPLY VACUUM TO A PRINTING NOZZLE TO PICK UP        │
│ AND DETACHABLY HOLD THE AT LEAST ONE TARGET         │
│ BIOLOGICAL ORGANISM FROM THE FIRST LOCATION         │─── 204
│ SUCH THAT AT LEAST A PORTION OF THE AT LEAST        │
│ ONE BIOLOGICAL ORGANISM REMAINS EXTERNAL TO         │
│ THE PRINTING NOZZLE                                 │
└─────────────────────────────────────────────────────┘
                          │
                          ▼
┌─────────────────────────────────────────────────────┐
│ IDENTIFY WITH THE IMAGE ACQUISITION SYSTEM A        │
│ SECOND LOCATION FOR DEPOSIT OF THE AT LEAST         │
│ ONE TARGET BIOLOGICAL ORGANISM, WHEREIN THE         │─── 206
│ FIRST LOCATION IS DIFFERENT FROM THE SECOND         │
│ LOCATION                                            │
└─────────────────────────────────────────────────────┘
                          │
                          ▼
┌─────────────────────────────────────────────────────┐
│ MOVE, WITH INPUT FROM THE IMAGE ACQUISITION         │
│ SYSTEM, THE ROBOTIC MOTION SYSTEM TO POSITION       │─── 208
│ THE PRINTING NOZZLE OF THE PLACEMENT HEAD AT        │
│ THE SECOND LOCATION                                 │
└─────────────────────────────────────────────────────┘
                          │
                          ▼
┌─────────────────────────────────────────────────────┐
│ APPLY A FLUID TO THE PRINTING NOZZLE TO DETACH      │
│ THE AT LEAST ONE TARGET BIOLOGICAL ORGANISM         │
│ FROM THE PRINTING NOZZLE AND DEPOSIT THE AT         │─── 210
│ LEAST ONE TARGET BIOLOGICAL ORGANISM AT THE         │
│ SECOND LOCATION                                     │
└─────────────────────────────────────────────────────┘
```

FIG. 4

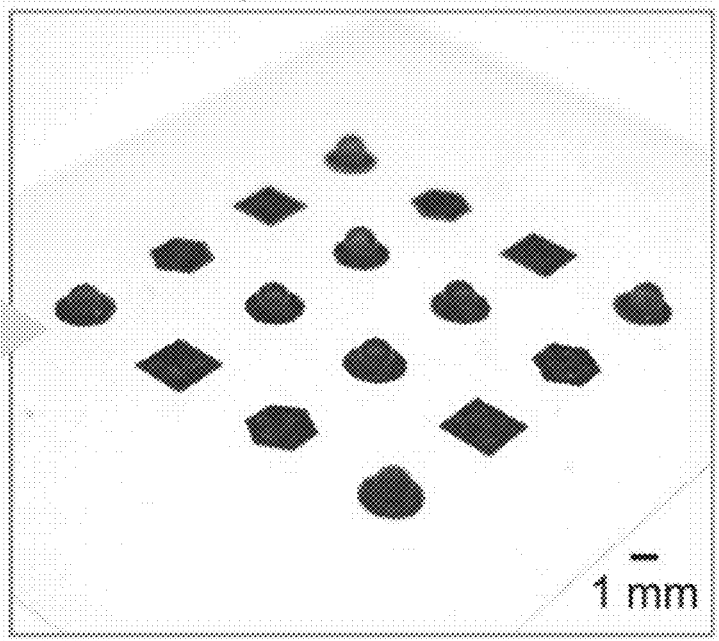
FIG. 15

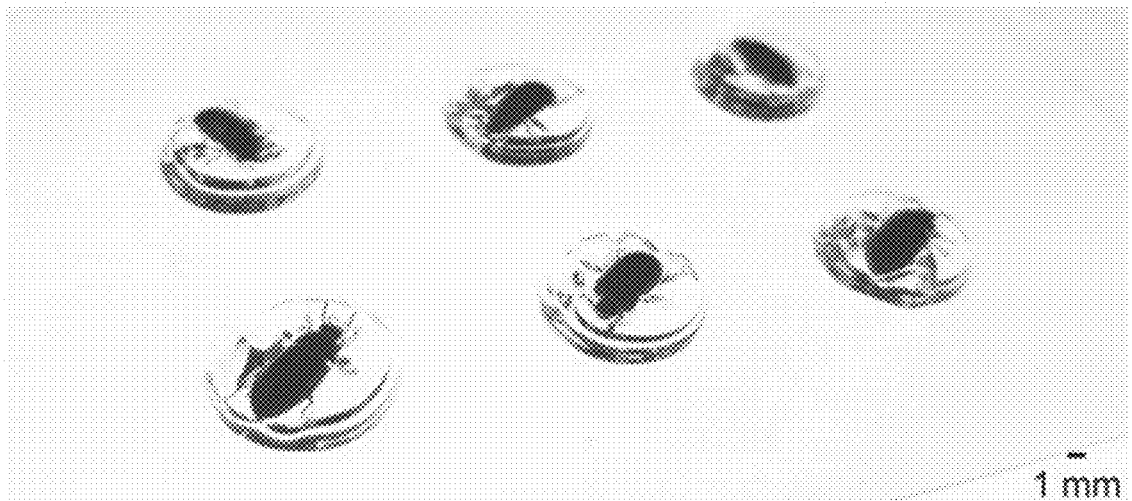
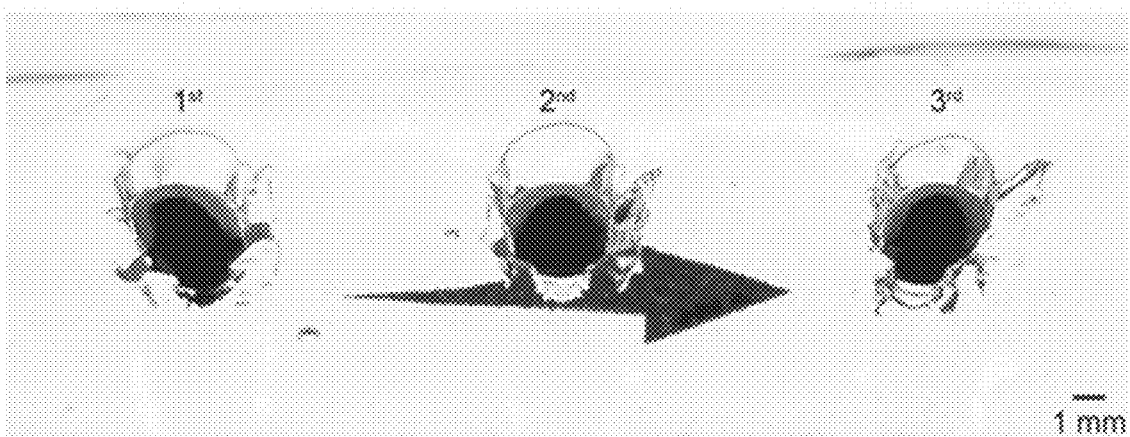
FIG. 23B

THREE DIMENSIONAL PLACEMENT OF ORGANISMS

This application claims the benefit of U.S. Provisional Patent Application No. 63/223,908, filed Jul. 20, 2021, the entire contents of which is incorporated herein by reference.

STATEMENT REGARDING FEDERALLY SPONSORED RESEARCH AND DEVELOPMENT

This invention was made with government support under MH122118 awarded by the National Institutes of Health. The government has certain rights in the invention.

This invention was made with government support under EEC-1941543 and IIP-1913772 awarded by the National Science Foundation. The government has certain rights in the invention.

BACKGROUND

In some processes such as, for example, cryogenic preservation, in vitro fertilization, tissue engineering, or multi-organism assembly, relatively large numbers of biological organisms are moved from a first location to a selected second location. In such processes target biological organisms are identified at the first location, manually placed in a liquid medium, and the liquid medium containing the biological organisms is drawn into a nozzle. The nozzle is then manually moved to the second location, and the liquid medium is dispensed from the nozzle to form a liquid droplet at the second location.

SUMMARY

In general, the present disclosure is directed to a system including a placement head with at least one printing nozzle configured to detachably retain and release at least one biological organism under a vacuum such that the biological organism remains at least partially outside the nozzle. An image acquisition system includes a visual inspection system that identifies at least one target biological organism to be picked up by the printing nozzle on the placement head in a first location, and a distance identification system (e.g., a triangulation system or a vertical distance detection system) that identifies a second location for deposit of the at least one target biological organism. A robotic motion system moves the placement head, based on input from the image acquisition system, from the first location to the second location. The target biological organism is then released from the printing nozzle and deposited at the second location.

At least a portion of the printing nozzles in the placement head include a screened tip with an orifice covered by a mesh screen. The mesh screen has an opening size selected to retain under vacuum a plurality of target biological organisms on an external surface of the screen, so the target biological organisms are not transported through the orifice, which can reduce or substantially eliminate orifice clogging. In some examples, at least a portion of the printing nozzles in the placement head are unscreened, but include an orifice with a diameter selected to retain an individual target organism under vacuum such that at least a portion of the individual target organism remains external to the tip of the nozzle during transport from the first location to the second location.

The motion system is moveable in two or three dimensions, and in some examples the image acquisition system includes a visual inspection system and a distance identification system utilizing light from an illumination source such as a laser. The distance identification system may be configured to determine vertical distances to the target organism and/or the substrate surface or a triangulation system that determines additional position information for the organism and/or target location. This integration of the printing nozzles with the visual inspection system and triangulation system improves throughput by making possible the rapid identification of target biological organisms at the first location, which are then rapidly moved and precisely deposited at the second location by the motion system using data from the image acquisition system.

The systems and methods of the present disclosure receive real-time information on the locations of randomly distributed biological organisms to be retrieved, and the locations and heights of target points where the organisms are to be deposited, via the visual inspection and distance identification system, such as laser triangulation systems. This real-time information exchange between system components enhances printing and pick-and-place throughput. In addition, in one example, the visual inspection system can be used to detect differences between desired and undesired target biological organisms at the first location. The systems and methods of the present disclosure can thus be used to pick and place biological organisms with high spatial resolutions, on non-planar surfaces, and with high throughput.

The systems and methods of the present disclosure can be used in a wide variety of applications such as, for example, to increase the throughput cryopreservation of organisms, to increase the throughput of parametric studies involving organisms, to sort different organisms and particles (e.g., dead, live, fertilized, and unfertilized embryos and undesired particles), to develop organism-based devices, and to develop ecosystems of organisms for farms.

In one aspect, the present disclosure is directed to a system that includes a placement head with at least one printing nozzle configured to pick up and detachably hold at least one biological organism; an image acquisition system including a visual inspection system that identifies at least one target biological organism to be picked up by the printing nozzle of the placement head in a first location, and identifies at least one second location for deposit of the at least one target biological organism, wherein the first location is different from the at least one second location; and a robotic motion system that moves the placement head, based on input from the visual inspection system and a distance identification system, from the first location to the at least one second location, such that the placement head deposits the target biological organism at the second location.

In another aspect, the present disclosure is directed to a method for moving at least one target biological organism from a first location to a second location. The method includes: identifying with a visual inspection system the at least one target biological organism at the first location to be picked up by a printing nozzle in a placement head, wherein the placement head is moveable in any of an x, y or a z direction with a robotic motion system; applying a vacuum to the printing nozzle to pick up and detachably hold the at least one target biological organism such that at least a portion of the at least one biological organism remains external to the printing nozzle; identifying with a distance identification system at least one second location for deposit of the at least one target biological organism, wherein the first location is different from the at least one second location; and moving, with input from the visual inspection system and the distance identification system, the robotic motion system to position the printing nozzle of the placement head at the at least one second location, and applying a fluid to the printing nozzle to detach the at least one target biological organism from the printing nozzle and deposit the at least one target biological organism at the at least one second location.

In another aspect, the present disclosure is directed to a printing head for depositing biological organisms. The printing head includes at least one meshed printing nozzle with an orifice overlain by a screen with a mesh having an opening size selected to retain under a vacuum a plurality of liquid-entrained biological organisms on an external surface of the screen; and at least one meshless printing nozzle with an orifice having a diameter of about 1 micron to about 3000 microns selected to retain under a vacuum an individual organism such that at least a portion of the individual organism is external to the tip.

In another aspect, the present disclosure is directed to a method for assembling organisms. The method includes: identifying with a visual inspection system the at least one target biological organism at a first location to be picked up by a nozzle in a printing head, wherein the printing head is moveable in any of an x, y or a z direction with a robotic motion system; applying a vacuum to the nozzle to pick up and detachably hold the at least one target biological organism such that at least a portion of the at least one biological organism remains external to the nozzle; identifying with a distance identification system at least one second location for deposit of the at least one target biological organism, wherein the first location is different from the at least one second location, and wherein a biological structure resides in the at least one second location; and moving, with input from the visual inspection system and the distance identification system, the robotic motion system to position the nozzle of the printing head at the at least one second location, and applying a fluid to the nozzle to detach the at least one target biological organism from the printing nozzle and deposit the at least one target biological organism on the biological structure at the at least one second location.

The details of one or more embodiments of the disclosure are set forth in the accompanying drawings and the description below. Other features, objects, and advantages of the disclosure will be apparent from the description and drawings, and from the claims.

BRIEF DESCRIPTION OF DRAWINGS

FIG. 1 is schematic diagrammatic view of an embodiment of a system for moving at least one target biological organism from a first location to at least one second location.

FIG. 2 is a schematic cross-sectional view of the operation of a meshed printing nozzle in the system of FIG. 1.

FIG. 3 is a schematic cross-sectional view of the operation of an unmeshed printing nozzle in the system of FIG. 1.

FIG. 4 is a flow chart of an embodiment of a method for moving a target biological organism from a first location to a second location.

FIG. 5 is a plot of survival rate vs. solution viscosity for the brine shrimp embryos of Example 2.

FIG. 6A includes photographs of target droplet deposition patterns used in Example 3.

FIG. 6B is a photograph of a non-planar surface used as a deposition substrate in Example 3.

FIG. 7 is a plot of survival rate vs. survival time for the zebrafish embryos of Example 3.

FIG. 8 is a conceptual diagram of an example system for moving static organisms.

FIG. 9 is a flow chart of an example method of operation of the system of FIG. 8.

FIG. 10 is a finite element-predicted color map of example stresses of an embryo under vacuum pressures.

FIG. 11 is a graph of survival rates of example embryos after the picking process.

FIG. 12 is a graph of example distances from the substrate for placing embryos.

FIG. 13 is a finite element-predicted color map of example stresses of an embryo during placement.

FIG. 14 is a graph of survival rates of example embryos after the picking and placement process.

FIG. 15 are example images of an example printing strategy.

FIG. 16 is a conceptual diagram of an example system for static and moving multiple organisms.

FIG. 17 is a flow chart of an example method of operation of the system of FIG. 16.

FIG. 18 is a graph of survival rates of example dinoflagellates after the printing process.

FIG. 19A is a graph of survival rates of example shrimp larvae after the picking and placing process.

FIG. 19B includes images of example organisms that can be moved using the system of FIG. 16.

FIG. 20 is a conceptual diagram of an example system for printing single moving organisms.

FIG. 21 is a flow chart of an example method of operation of the system of FIG. 20.

FIG. 22 is a graph of the trajectory of beetles printed in pluronic hydrogel as a function of time and thickness of the hydrogel.

FIG. 23A is a graph of survival rates of example beetles after the picking and placing process.

FIG. 23B includes images of example organisms that can be moved using the system of FIG. 20.

FIG. 24 is a graph of survival rates of example cryopreserved embryos after the printing process.

FIG. 25 is a graph of the example throughput of manual manipulation versus 3D printing process.

FIG. 26 is a graph of the relation between droplet volume and cryopreservation parameters.

Like symbols in the drawings indicate like elements.

DETAILED DESCRIPTION

This disclosure describes systems, devices, and techniques related to automatically identifying and moving biological organisms using a placement head where the biological organisms remain at least partially outside of the nozzle. In one example, a system includes a placement head with at least one printing nozzle configured to detachably retain and release at least one biological organism under a vacuum such that the biological organism remains at least partially outside the nozzle. Generally, relatively small biological organisms can be moved manually using a liquid medium in which a nozzle draws in the medium, is moved to a new location, and then the liquid medium is dispensed from the nozzle to form a liquid droplet at the new location.

However, when performed manually, these processes are slow and cumbersome, and often result in clogging of the delivery nozzle. To reduce nozzle clogging, the diameter of the nozzle orifice can be increased, but increasing nozzle diameter results in larger droplets at the second location that contain fewer biological organisms per unit droplet volume, and such low throughput and poor spatial resolution are not acceptable in procedures that require large numbers of biological organisms to be transported in a short period of time or stored in a relatively small storage space. The larger droplets also provide relatively poor scalability in handling processes for biological organisms. These problems have slowed the adoption of high-throughput and high-resolution processes such as, for example, three-dimensional (3D) pick and place and 3D printing, to the transport and precision placement of biological organisms.

As described herein, the present disclosure is directed to systems and techniques for detachably retaining biological organisms and imaging systems that enable the nozzle to move from one location to another. In some examples, the system includes a placement head with at least one printing nozzle configured to detachably retain and release at least one biological organism under a vacuum such that the biological organism remains at least partially outside the nozzle. An example image acquisition system includes a visual inspection system that identifies at least one target biological organism to be picked up by the printing nozzle on the placement head in a first location, and a distance identification system, such as a triangulation system or height measurement system, that identifies a second location for deposit of the at least one target biological organism. In other examples, the visual inspection system may include a vision system and laser system that provides location information used to identify the organisms and target locations to move the organisms. A robotic motion system moves the placement head, based on input from the image acquisition system, from the first location to the second location. The target biological organism is then released from the printing nozzle and deposited at the second location.

In some examples, at least a portion of the printing nozzles in the placement head include a screened tip with an orifice covered by a mesh screen. The mesh screen can have an opening size selected to retain under vacuum a plurality of target biological organisms on an external surface of the screen, so the target biological organisms are not transported through the orifice, which can reduce or substantially eliminate orifice clogging. In some examples, at least a portion of the printing nozzles in the placement head are unscreened, but include an orifice with a diameter selected to retain an individual target organism under vacuum such that at least a portion of the individual target organism remains external to the tip of the nozzle during transport from the first location to the second location.

The motion system can be moveable in two or three dimensions, and in some examples the image acquisition system includes a visual inspection system and a distance identification system (e.g., a triangulation system or height detection system) utilizing light from an illumination source such as a laser. This integration of the printing nozzles with the visual inspection system and triangulation system improves throughput by making possible the rapid identification of target biological organisms at the first location, which are then rapidly moved and precisely deposited at the second location by the motion system using data from the image acquisition system.

The systems and methods of the present disclosure receive real-time information on the locations of randomly distributed biological organisms to be retrieved, and the locations and heights of target points where the organisms are to be deposited, via the visual inspection and distance identification systems. This real-time information exchange between system components enhances printing and pick-and-place throughput. In addition, in one example, the visual inspection system can be used to detect differences between desired and undesired target biological organisms at the first location. The systems and methods of the present disclosure can thus be used to pick and place biological organisms with high spatial resolutions, on non-planar surfaces, and with high throughput.

The systems and methods of the present disclosure can be used in a wide variety of applications such as, for example, to increase the throughput cryopreservation of organisms, to increase the throughput of parametric studies involving organisms, to sort different organisms and particles (e.g., dead, live, fertilized, and unfertilized embryos and undesired particles), assist disease research, develop therapies, to develop organism-based devices, and to develop ecosystems of organisms for farms).

Referring now to FIG. 1, a schematic illustration (which is not to scale) of a system 10 includes a robotic motion system 12 including substantially parallel tracks 14 traversed by a crossmember 16. The crossmember 16 includes a placement or printing head 18, which is moveable in any of the x, y or z directions over a surface 20 of a substrate 22. The printing head can be moved to precise locations on the surface 20 upon receipt of location information from a controller 100.

The placement head 18 includes at least one printing nozzle 30, which is connected to a vacuum and dispensing system 24 by at least one vacuum line 26. The printing nozzle 30 includes a body 31 with an internal passage 35 (not shown in FIG. 1, please see FIG. 2) leading to a tip 33. The tip 33 includes a nozzle 32 with an orifice 34. The orifice 34 is covered by a screen 36, which overlies the orifice 34. While FIG. 1 illustrates an embodiment of the system 10 including a single vacuum and dispensing system 24, in other examples multiple vacuum and dispensing systems can be used to supply one or more individual nozzles on the placement head 18.

As shown schematically in FIG. 2, the screen 36 has a mesh having an opening size selected to retain, under a vacuum from the vacuum system 24, a plurality of target biological organisms 50 on an external surface 38 of the screen 36 such that the target biological organisms 50 do not enter the orifice 34. In the embodiment of FIG. 2, the target biological organisms 50 are lifted away from a first location 52 on the surface 20 of the substrate 22 when a vacuum is applied to the printing nozzle 30. In some examples, adhesives, hydrogels, grippers, hook and loop fasteners such as those available under the trade designation VELCRO from Velcro Companies, Manchester, NH, clamps, and soft robotic manipulators are used to lift away the target biological organisms 50. In some examples, the substrate 22 includes an illumination source.

As shown in FIG. 2, the plurality of target biological organisms 50 are lifted away from the first location 52 in a liquid state, a substantially liquid-free state, or in a liquid-free state, and are retained in contact with the exposed surface 38 of the screen 36. In this application, the term liquid state means that the target biological organisms 50 include less than about 100% by weight of a liquid when adhered to the external 38 of the screen 36. The term substantially liquid free means that the target biological organisms 50 include less than about 50% by weight, or less than about 10% by weight, of a liquid when adhered to the external surface 38 of the screen 36. The term liquid free in this application means that the target biological organisms 50 include less than 5% by weight, or less than 1% of liquid when adhered to the external surface 38 of the screen 36.

In some examples, which are not intended to be limiting, the opening size in the mesh of the screen 36 is about 1 micron to about 3000 microns. In another example, the screen 36 has an open area percentage of about 1% to about 99%. In some examples, which are not intended to be limiting, the screen is formed from a metal, a polymeric material, a ceramic material, a hydrogel material, or a biological material.

Referring again to FIG. 2, after the printing nozzle 30 is moved by the placement head 18 from the first location 52 to a selected second location or locations 54, a fluid (for example, air) is applied to the printing nozzle 30 by the vacuum and dispensing system 24 to release the target biological organisms 50 from the surface 38 of the screen 36. The target biological organisms 50 are deposited at the at least one second location 54 in a droplet 56 of a liquid medium. In some examples, the droplet 56 includes less than about 100 µL, or less than about 5 µL, or less than about 1 µL of the liquid medium. In some examples, the liquid medium in the droplet 56 can include water, or aqueous solutions including additives such as, for example, poly (ethylene glycol) (PEG), nanoparticles, or hydrogels. For example, in some embodiments the liquid medium in the droplet 56 is an aqueous solution with about 10 wt %, or about 20 wt %, PEG. In another embodiment, if the target biological organisms 50 are to be cryopreserved, the liquid medium in the droplet 56 can include cryoprotectant agents such as, for example, dimethylformamide (DMF), or dimethyl sulfoxide (DMSO).

FIG. 2, which is not to scale, shows a relatively small number of target biological organisms 50 in the droplet 56. However, in some examples, the droplet 56 can include about 10, 20, 30, 40 or even 300 of the target biological organisms 50. The number of target biological organisms 50 per unit droplet volume at the second location 54 can be controlled by adjusting the vacuum time and level with the vacuum and dispensing system 24.

As shown schematically in FIG. 2, in some examples the meshed printing nozzle 30 can optionally include a cleaning nozzle 40 to remove residual liquid medium surrounding the tip 33 and the orifice 34 to create a droplet 56 with target biological organisms 50.

Referring again to FIG. 1, the placement head 18 can optionally also include an unmeshed printing nozzle 60. The unmeshed printing nozzle 60 includes a body 61 with a tip 63, a nozzle 62, and an orifice 64. Since the unmeshed printing nozzle 60 does not include a mesh covering over the orifice 64, the orifice 64 has a diameter selected to retain an individual target organism under vacuum from the vacuum and dispensing system 24 such that at least a portion of the individual target organism remains external to the tip 63. In some examples, the orifice 34 of the unmeshed printing nozzle 60 has a diameter of about 1 micron to about 3000 microns.

Referring now to the schematic diagram in FIG. 3, when vacuum is applied to the tip 63 of the printing nozzle 60 via a passage 65 therethrough, a single target biological organism 50 is lifted away from a first location 52 on the surface 20 of the substrate 22. The target biological organism 50 is retained in the orifice 64 of the nozzle 62 such that a portion of the target biological organisms 50 remains outside the tip 63 and the organism 50 does not fully enter the orifice 64. In some examples, adhesives, hydrogels, grippers, hook and loop fasteners, clamps and soft robotic manipulators are utilized to pick up the single target biological organisms 50.

The single target biological organism 50 is lifted away from the first location 52 in a liquid state, or a substantially liquid-free state, or in a liquid-free state, and is retained within the orifice 64. After the printing nozzle 60 is moved by the placement head 18 from the first location 52 to a selected second location 54 on the surface 20 of the substrate 22, a fluid (for example, air) is applied to the printing nozzle 60 by the vacuum and dispensing system 24 to release the target biological organism 50 from the nozzle 64. The target biological organism 50 is deposited at the second location 54 in a droplet 56 of a liquid medium, which as in FIG. 2 above has a volume of liquid medium of less than about 100 µL, or less than about 1 µL, or less than about 0.1 µL.

Referring again to FIG. 1, in some examples the placement head 18 can optionally include a fluid delivery nozzle 70, which may be used to apply an additional fluid from a fluid source 71 to the first location 52, the second location 54, or the droplet 56 (FIGS. 2-3) by applying pressure with the vacuum and dispensing system 24. For example, the additional fluid dispensed from the fluid delivery nozzle 70 may be used for further processing of the target biological organisms in the first location 52, the second location 54, or the droplet 56. In some examples, which are not intended to be limiting, the additional fluids can include drugs, growth agents, cryoprotectant agents, nanoparticles, stains or other colorants.

In some example, the placement head 18 can further include an illumination source 72 that casts light on all or a portion of the surface 20 of the substrate 22 or is utilized to measure height profiles of objects on the surface 20 of the substrates 22. Any suitable source of light can be used, and in some examples the illumination source 72 includes at least one laser emitting a beam 73 onto the surface 20 to measure the profiles of the surface or object point by point. In some examples, the laser in the illumination source 72 may be a visible light laser diode, and optics in the illumination source (not shown in FIG. 1) may be used to focus the beam 73 onto the substrate 20. In some examples, the substrate 20 includes an illumination source.

As shown in FIG. 1, the system 10 further includes a camera 80 with a lens system 82. In some embodiments, the camera 80 is a 2-D complementary metal oxide semiconductor (CMOS) or charge-coupled device (CCD) device, which is used by the system 10 as a sensor. While the camera 80 and the illumination source 72 are shown as separate components in the schematic of FIG. 1, in some examples, all of these elements can be incorporated into a single, sealed enclosure, to create a sensor head or vision system. In some examples, the illumination source 72 separately measures profiles of a surface and an object based on the location detected by the camera 80 and vision system, and the substrate 20 acts as an illumination source. The camera 80 receives input from the controller 100, as further explained below.

Referring again to FIG. 1, the controller 100 includes at least one processor 102 configured to process detected signals from one or more sensor systems 104 in the system 10. In some examples, the processor 102 may be integrated with the sensor systems 104, may be integrated with the controller 100, or may be a remote processor functionally connected to the controller 100.

The processor 102 may be any suitable software, firmware, hardware, or combination thereof. The processor 102 may include any one or more microprocessors, controllers, digital signal processors (DSPs), application specific integrated circuits (ASICs), field-programmable gate arrays (FPGAs), or discrete logic circuitry. The functions attributed to the processor 102 may be provided by processing circuitry of a hardware device, e.g., as supported by software and/or firmware.

In some examples, the processor 102 may be coupled to a memory device 110, which may be part of the controller 110 or remote thereto. The memory device 110 may include any volatile or non-volatile media, such as a random-access memory (RAM), read only memory (ROM), non-volatile RAM (NVRAM), electrically erasable programmable ROM (EEPROM), flash memory, and the like. The memory device 110 may be a storage device or other non-transitory medium. The memory device 110 may be used by the processor 102 to, for example, store fiducial information or initialization information corresponding to, for example, movement patterns or locations of the placement head 18, surface geometries of the surface 20 of the substrate 22, locations of target biological organisms on the surface 20, locations or shapes of droplets on the surface 20, measurements or stored signals from the sensor system 104, operation of the camera 80 and the illumination source 72, and the like. In some examples, the memory device 110 may store determined values, such as, for example first and second locations on the substrate 20 where the target biological organisms are to be picked up or released by the nozzles 30, 60, where and how much fluid is to be applied to a location on the surface 20 by the fluid delivery nozzle 70, and the like, for later retrieval.

In some embodiments, the controller 100 and the processor 102 are coupled to a user interface 112, which may include a display, user input, and output (not shown in FIG. 1). Suitable display devices include, for example, monitor, PDA, mobile phone, tablet computers, and the like. In some examples, user input may include components for interaction with a user, such as a keypad and a display such as a cathode ray tube (CRT) display, a liquid crystal display (LCD) or light emitting diode (LED) display, and the keypad may take the form of an alphanumeric keypad, or a reduced set of keys associated with particular functions. In some examples, the displays may include a touch screen display, and a user may interact with user input via the touch screens of the displays. In some examples, the user may also interact with the user input remotely via a networked computing device.

As noted above, the controller 100 can be configured to control any selected number of functions of the system 10 including, but not limited to, movements of the placement head 18, movement patterns for the individual printing nozzles 30, 60, control of the vacuum and dispensing system 24, and the like, in response to signals from the processor 102 input manually into the controller 100, or stored in the memory device 110. For example, in some embodiments, the controller may be used to mathematically reconstruct the target surface geometry and design the routing and geometry of patterns of droplets on the surface 20, and may be used to recognize droplets in any desired pattern on the surface 20.

In some examples, the controller 100 can be configured to generate control signals obtained from, for example, one or more sensors in the sensor system 104, to provide closed loop control of the movements of the placement head 18 and the printing nozzles 30, 60. In some examples, the sensor system 104 includes a visual inspection system 106 that acquires and processes images to detect objects and features on the surface 20 to analyze and determine characteristics in the objects or other features detected in the images. A camera/frame grabber system generates images that are then processed with an algorithm implemented in software.

The visual inspection system 106 is programmable and provides customized automated video inspection. The software in the visual inspection system allows an automatic inspection sequence to be defined by the user for each configuration on the surface 20. The visual inspection system 106 may be used to simplify and increase the throughput of the system 10 to the extent that the operation of the system 10 proceeds reliably and repeatedly. The results of the various inspection operations performed by the visual inspection system 106 can also be stored within the visual inspection system 106 itself or with the memory device 110 in the controller 100.

In some examples, the vision inspection system 106 includes search tools that provide pattern matching and searching. For example, the machine vision of the vision inspection system 106 can be used to determine the location of a fiducial, a mark, an object (for example, a specific type of one or more target biological organisms, or a specific type of living target biological organism, a specific type of droplet of a liquid medium, and the like), or other "template" in an image. The search tools of the vision system 106 enable a previously stored image pattern to be acquired and registered/identified regardless of its viewed position. The machine vision tools in the system 106 acquire an image of a pattern via the camera 80 and analyze the outline or a particular part of the pattern. For example, the machine vision of the vision system 106 may be used to identify living target biological organisms among a mixture of living and dead organisms in an organism reservoir, pick specific types of organisms from a mixture of organisms or a mixture of organisms and other debris, or identify fertilized embryos from a mixture of fertilized and unfertilized embryos.

In some embodiments, the sensor system 104 further includes additional machine vision hardware or software 108 that includes a distance identification system (e.g., a laser triangulation system or sensor) to capture 2-dimensional, or 3-dimensional measurements by pairing the laser illumination source 72 with the camera 80. In one example, if the laser beam 73 and the camera 80 are both directed toward the surface 20 of the substrate 22, adopting a known angular offset between the laser source 72 and the camera sensor 80, a laser triangulation system can be used to measure depth differences on the surface 20, or measure a single point distance on the surface 20, or even to obtain a point-by-point profile scan or surface scan of the surface 20. The laser triangulation system is an example of a distance identification system. In other examples, the distance identification system is configured to determine distances associated with target organisms and/or surface of the substrate (e.g., heights) in order to determine the precise location of the organisms and assist in picking and placement of the organisms at the target location(s). In this manner, the distance identification system may be configured to determine 2-dimensional distances of objects or structures of interest (e.g., the height of the organism or substrate in the Z-direction) or 3-dimensional positions in the x, y, and z directions.

In various examples, the controller 100 may be adjusted by a variety of manual and automatic means. Automatic means may make use of any number of control algorithms or other strategies to conform to a controlled deposition pattern or procedure for the target biological organisms manipulated by the printing nozzles 30, 60 on the placement head 18, For example, standard control schemes as well as adaptive algorithms such as so-called "machine-learning" algorithms may be used. In some examples, the controller 100 can utilize information from other sources not shown in FIG. 1 such as, for example, infrared cameras, to determine the control action decided by algorithms or other machine learning schemes.

While the schematic depiction in FIG. 1 shows the substrate 22 and the surface 20 to be relatively flat and planar, the system 10 may be used to deposit a target biological organism on any type of surface including, for example curved surfaces, edges, or even compound surfaces. The surface 20 in some embodiments may be non-planar such as for example, arcuate, curvilinear, spherical and the like. The substrate 22 and the surface 20 may be formed from a wide variety of materials, and in various embodiments, which are not intended to be limiting, can be glass, a polymeric film, a metal, a surface of an electronic component such as, for example, a silicon wafer, a fabric, human or animal skin, soft hydrogels, and the like.

In another aspect, the present disclosure is directed to a method for moving at least one target biological organism from a first location on a substrate to a second location on the same or a different substrate. Referring now to FIG. 4, the method 200 includes an initial step 202 identifying with an image acquisition system at least one target biological organism at the first location to be picked up by a printing nozzle in a placement head, wherein the placement head is moveable in any of an x, y or a z direction with a robotic motion system.

In step 204, the method includes applying a vacuum to the printing nozzle to pick up and detachably hold the at least one target biological organism such that at least a portion of the at least one biological organism remains external to the printing nozzle. In some examples, adhesives, hydrogels, grippers, hook and loop fasteners, clamps, and soft robotic manipulators are utilized to pick up the target biological organisms.

In step 206, the method includes identifying with the image acquisition system a second location for deposit of the at least one target biological organism, wherein the first location is different from the second location.

Step 208 of the exemplary method includes moving, with input from the image acquisition system and laser displacement sensor, the robotic motion system to position the printing nozzle of the placement head at the second location.

In step 210, the method includes applying a fluid to the printing nozzle to detach the at least one target biological organism from the printing nozzle and deposit the at least one target biological organism at the second location.

In the present application the term biological organism can refer to, but is not limited to, embryos, larvae, insects, mammals, fish, birds, reptiles, amphibians, trees, herbs, bushes, grasses, vines, ferns, mosses, green algae, and the like.

The systems and methods of the present disclosure can be used in a wide variety of applications such as, for example, to increase the throughput cryopreservation of organisms, to increase the throughput of parametric studies involving organisms, to sort different organisms and particles (e.g., dead, live, fertilized, and unfertilized organisms and undesired particles), to develop organism-based devices, and to develop ecosystems of organisms for farms.

In one example, the systems and method of the present disclosure can have sufficient resolution to deposit a target biological organism at a location on a substrate that is already occupied by another biological organism or collection of biological organisms. Placing layers of biological organisms in layers on top of each other can be useful in the development of mini ecosystems with living organisms and organism cryopreservation.

The systems and techniques described here can provide the ability to place living organisms with functional materials in desired 3D spaces and can have numerous uses in areas such as cryopreservation, disease research, development of therapies, and the creation of organism-based devices. These systems can operate to continuously assess the locations of randomly oriented living and moving organisms so some or all of the organisms can be collected and transferred to desired 3D spaces without damage in a high-throughput manner. In some examples, the systems can interweave functional materials with the organisms. Manual performance of these functions but have inconsistent levels of accuracy and are not able to handle hazardous materials. To overcome these barriers, the systems and techniques described herein can use a multi-nozzle 3D printing system that can identify and judge living and moving organisms and place them with functional materials in 3D spaces. Vacuum-assisted nozzles can be configured to print single and multiple organisms, and these nozzles are more controllable than human hands. The multi-nozzle 3D printing system can be enhanced by the integration of vision and laser systems, which enable the system to continuously adapt to newly updated information about randomly oriented organisms and target locations. Various examples include 3D printing of organisms with functional materials that can enhance the throughput of organism cryopreservation and organism-related studies and/or enable novel study designs and devices with organisms. In some examples described herein, example 3D printing systems can position various organisms in target locations with testbeds of various organisms, such as zebrafish embryos, dinoflagellates, shrimp embryos, shrimp larvae, and beetles.

As generally described herein, systems and techniques may be configured to acquire spatial information about target organisms and substrates via a combination of vision (e.g., visual inspection) and laser (e.g., distance identification) systems. A vision system, such as machine vision, can be configured to detect the 2D locations of target organisms and substrates and judge their conditions and shapes. Then, the laser system can be configured to be automatically located on top of the target organisms and substrates based on the vision information and measure the organism and/or substrate profiles (e.g., heights). The system can also use the spatial information from the vision and laser systems to guide a multi-nozzle 3D printer to position organisms in target 3D spaces and, in some examples, print substances, such as fluid (e.g., cryoprotectant droplets) and/or solids (e.g., electrodes, hydrogel, and devices), elements on the target organisms.

The devices of the present disclosure will now be further described in the following non-limiting examples.

EXAMPLES

Example 1

The device of FIG. 1, including one meshed printing nozzle 30, was used to move multiple brine shrimp embryos from a reservoir and place the embryos in droplets on cantilevered structures (cryotops) with random orientations and heights.

Example 2

The device of FIG. 1, including one meshed printing nozzle 30, was used to move multiple brine shrimp embryos from a reservoir and place the embryos in droplets having various viscosities and compositions. As shown in the plot of FIG. 5, the embryos were placed in seawater, as well as in aqueous solutions with 10% poly(ethylene glycol) (PEG) and 20% PEG.

The plot of FIG. 5 also shows that the printing process did not affect the survival rates of the organisms.

Example 3

The 3D printing stage of FIG. 1, combined with the mesh-less printing nozzle 60, automatically sensed the locations of randomly oriented single zebrafish embryos in a reservoir using the vision system, picked up the single embryos under a vacuum, and deterministically printed the embryos in desired 3D spaces automatically detected by the vision and laser system. As shown in FIG. 6A, the system was utilized to place the embryos in circles with a selected shape, and in FIG. 6B the embryos were printed on a curved substrate.

As shown in the plot of FIG. 7, the printing process did not affect the survival rate of the embryos compared to the survival rate of a control sample.

Example 4

FIG. 8 is a conceptual diagram of an example system 250 for moving static organisms. System 250 may be similar to system 10 of FIG. 1 and printing nozzle 60 of FIG. 3. System 250 includes 3D printer nozzle 254, vision system 252, and laser system 256. 3D printer nozzle 254 is configured to pick up organisms 262 from within liquid 258 (e.g., water) within container 260 via the location assistance of vision system 252. Using information acquired by vision system 252 and laser system 256, 3D printer nozzle 254 can place organisms 262 at a respective target mark 266. System 250 can differentiate from non-target marks 268. Laser system 256 may be referred to as a distance identification system and can emit a laser beam 257 that is used to determine distances that system 250 uses to control the movement of 3D printer nozzle 254 to the appropriate location on substrate 264 and at the appropriate height. In this manner, system 250 is configured to pick up randomly distributed single organisms and place the single organisms at respective desired locations, such as on target marks 266.

System 250 can be used with organisms of various elastic moduli and length, such as flexible and small organisms less than 0.5 millimeters in diameter like shrimp larva to more rigid and larger organisms such as beetles with hard exoskeletons. 3D printer nozzle 254 may create vacuum pressure that causes the distal end of 3D printer nozzle 254 to retain the target organism until the vacuum pressure is released. Example vacuum pressure can range from below 2.5 kPa to above 4.0 kPa.

FIG. 9 is a flow chart of an example method of operation of the system of FIG. 8. As shown in technique 300, system 250 can detect randomly oriented single organisms based on information from vision system 252 (302). System 250 can then control 3D printing nozzle 254 to move and pick up the single organism with the vacuum assisted nozzle (304). System 250 can then place the organism, or multiple organisms, in desired 3D spaces with the nozzle based on real-time information from the 3D printer, vision system 254, laser system 256, and/or prescribed coordinates from the 3D printer controlling 3D printer nozzle 254 (306). System 250 can then remove residual water from the nozzle (308).

FIG. 10 is a finite element-predicted color map of example stresses of an embryo under vacuum pressures. The finite element predicted stress distribution of chorion envelope of embryos is shown in the example of FIG. 10. These stresses can be caused by the vacuum created by 3D printer nozzle 254. The highest stresses may occur at the organism in physical contact with the outlet of printer nozzle 254.

FIG. 11 is a graph of survival rates of example embryos after the picking process, where (t1=0.5 s, t2=1 s, t3=2 s, and t4=3 s) and (n=30). System 250 did not decrease survival rates of organisms consistent with the control group that did not go through any manipulation.

FIG. 12 is a graph of example distances from the substrate for placing embryos. In the example of FIG. 12, the distances between the end of the nozzle and the substrate is shown for effective contact with the organism and where the organism bursts. Although this distance may be different for different organisms, system 250 can control the distance of 3D printer nozzle from substrate 264, for example, to enable intact placement of organisms while reducing the possibility of bursting.

FIG. 13 is a finite element-predicted color map of example stresses of an embryo during placement. In the example of FIG. 13, example finite element predicted stress distribution of chorion envelope of embryos is shown caused by 3D printer nozzle 254 during placing. As shown, the larger stresses are caused on the portions of the organism outside of the nozzle.

FIG. 14 is a graph of survival rates of example embryos after the picking and placement process over 1 day, 2 days, and 3 days. System 250 did not decrease survival rates of organisms consistent with the control group that did not go through any manipulation.

FIG. 15 are example images of an example printing strategy. As shown in the example of FIG. 15, system 250 can employ a printing strategy that can automatically position randomly distributed embryos in target marks (e.g., circular target marks) instead of non-target marks (e.g., squares and hexagons) by using their newly updated spatial location information via vision system 252 and laser system 256.

Example 5

FIG. 16 is a conceptual diagram of an example system for static and moving multiple organisms. System 350 may be similar to system 10 of FIG. 1, printing nozzle 30 of FIG. 2, and system 250 of FIG. 8. System 350 includes 3D printer nozzle 352, vision system 252, and laser system 256. 3D printer nozzle 352 is a mesh-filtered nozzle and includes a mesh 354 covering the inlet of the nozzle. 3D printer nozzle 352 is configured to pick up organisms 362 from within liquid 360 via the location assistance of vision system 252. 3D printer nozzle 352 may pick up multiple organisms 362 at the same time as they are held against the mesh 354. Using information acquired by vision system 252 and laser system 256, 3D printer nozzle 352 can place organisms 362 within organism-laden droplet 366 at a respective target substrate 364. Laser system 256 may be referred to as a distance identification system and can emit a laser beam 257 that is used to determine distances that system 350 uses to control the movement of 3D printer nozzle 352 to the appropriate location on substrate 364 and at the appropriate height. In this manner, system 350 is configured to pick up randomly distributed multiple organisms and place the organisms at respective desired locations on target substrate 364.

System 350 can be used with organisms of various elastic moduli and length, such as flexible and small organisms less than (and greater than) 0.25 millimeters in diameter like shrimp larva to more rigid and larger organisms such as beetles with hard exoskeletons. In some example, system 350 can move organisms contained within droplets less than (and greater than) 1 micro liter in volume. Example organisms include dinoflagellates, shrimp embryos, and shrimp larva. 3D printer nozzle 352 may create vacuum pressure that causes the distal end of 3D printer nozzle 352 to retain the target organisms against mesh 354 until the vacuum pressure is released.

FIG. 17 is a flow chart of an example method of operation of the system of FIG. 16. As shown in technique 380, system 350 can detect a reservoir including multiple organisms based on real-time information (e.g., from vision system 252 and the 3D printer) and/or prescribed coordinates of the nozzle (e.g., from the 3D printer) (382). System 350 can then control 3D printing nozzle 352 to move and pick up multiple organisms with the vacuum assisted nozzle (384). System 350 can then place the multiple organisms in desired 3D spaces with the nozzle based on real-time information from the 3D printer, vision system 254, and/or laser system 256 and/or prescribed coordinates from the 3D printer controlling 3D printer nozzle 352 (386). System 350 can then remove residual liquid from the nozzle (388).

Figure 16:
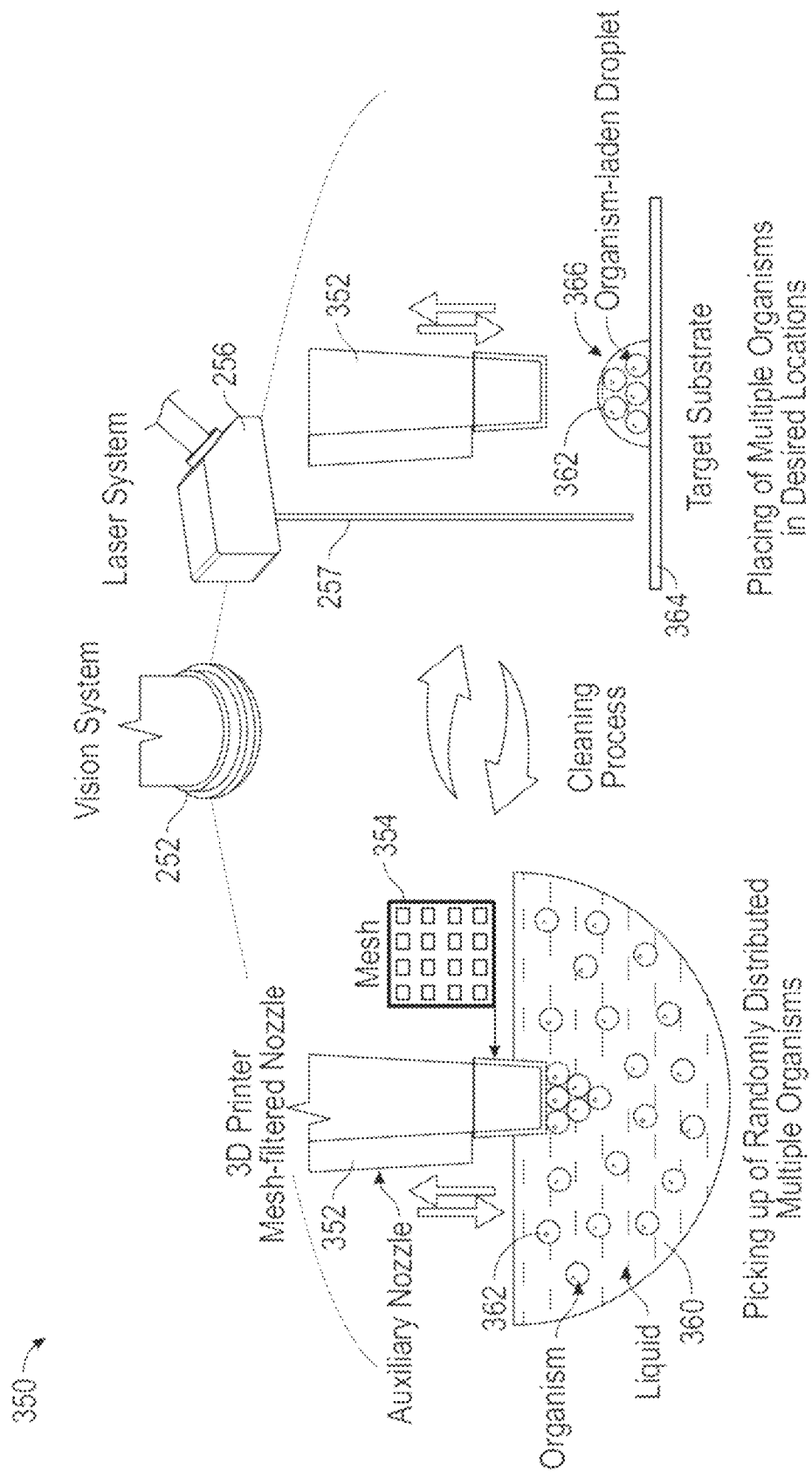
Figure 17:
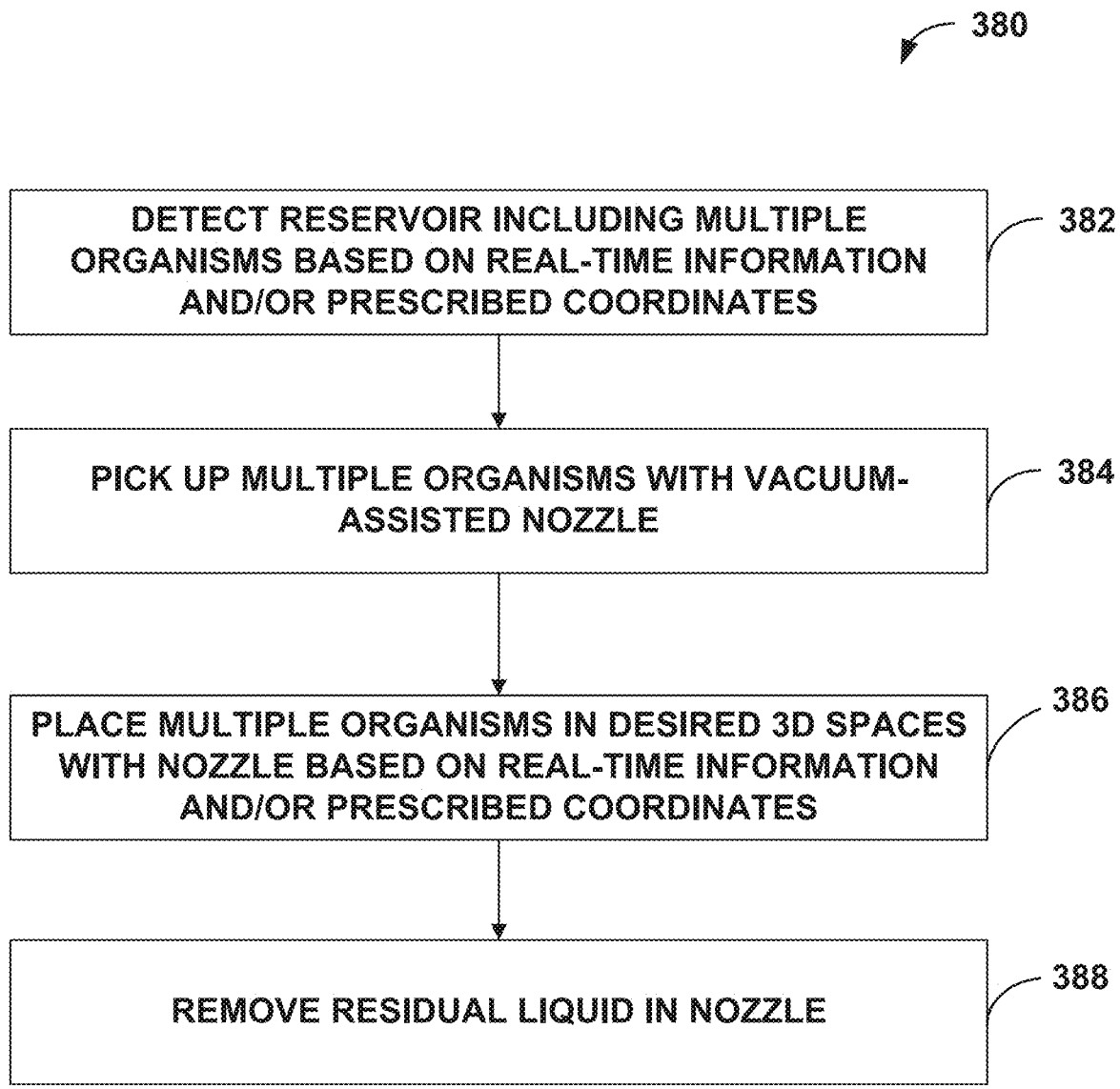
Figure 18:
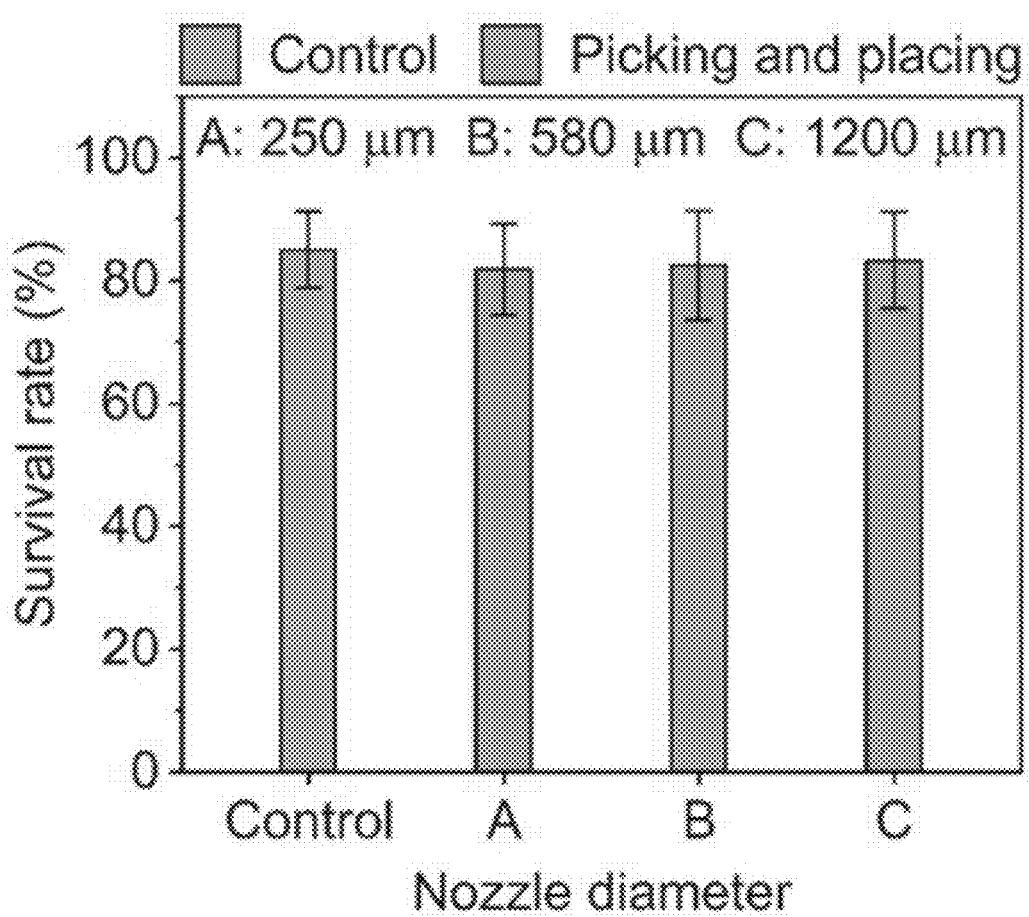
FIG. 18 is a graph of survival rates of example dinoflagellates after the printing process using nozzles having diameters of 250 micrometers, 580 micrometers, and 1200 micrometers. System 350 did not decrease survival rates of organisms consistent with the control group that did not go through any manipulation.
Figure 19A:
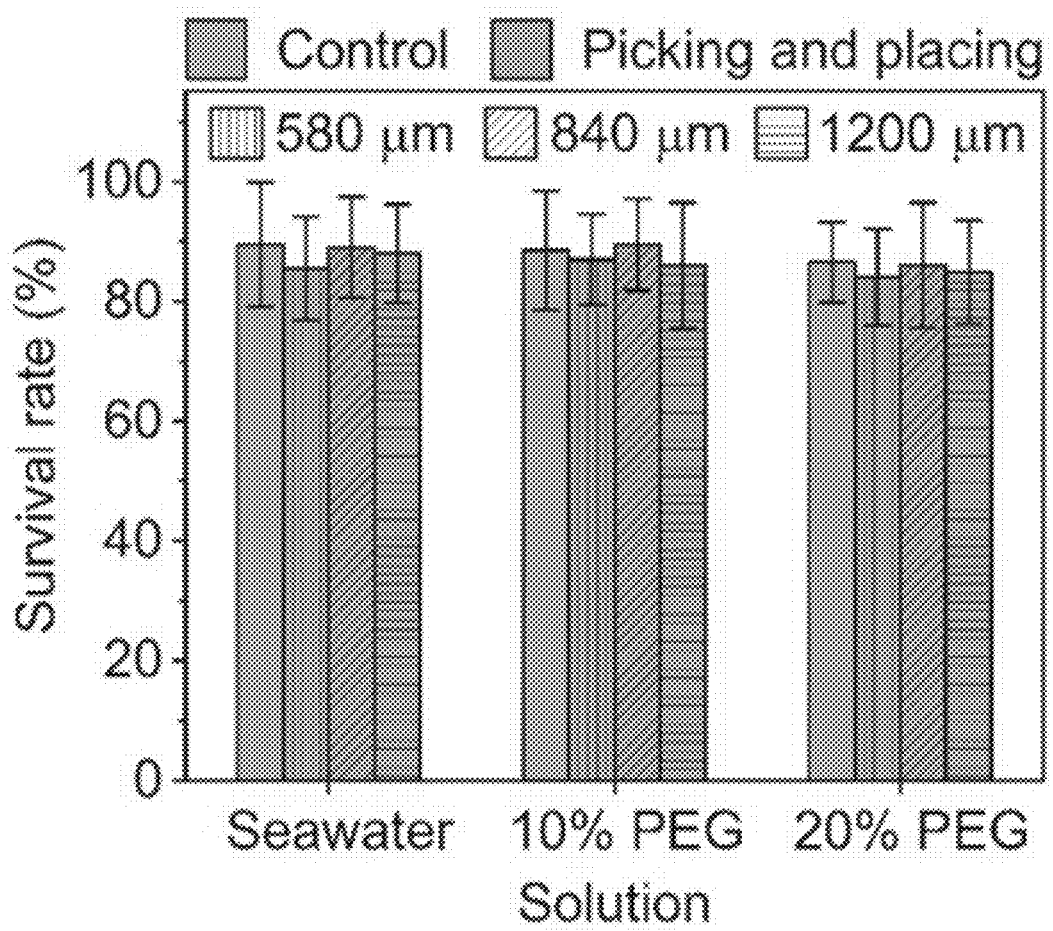
FIG. 19A is a graph of survival rates of example shrimp larvae after the picking and placing process using nozzles having diameters of 250 micrometers, 580 micrometers, and 1200 micrometers. System 350 did not decrease survival rates of organisms consistent with the control group that did not go through any manipulation.
Figure 19B:
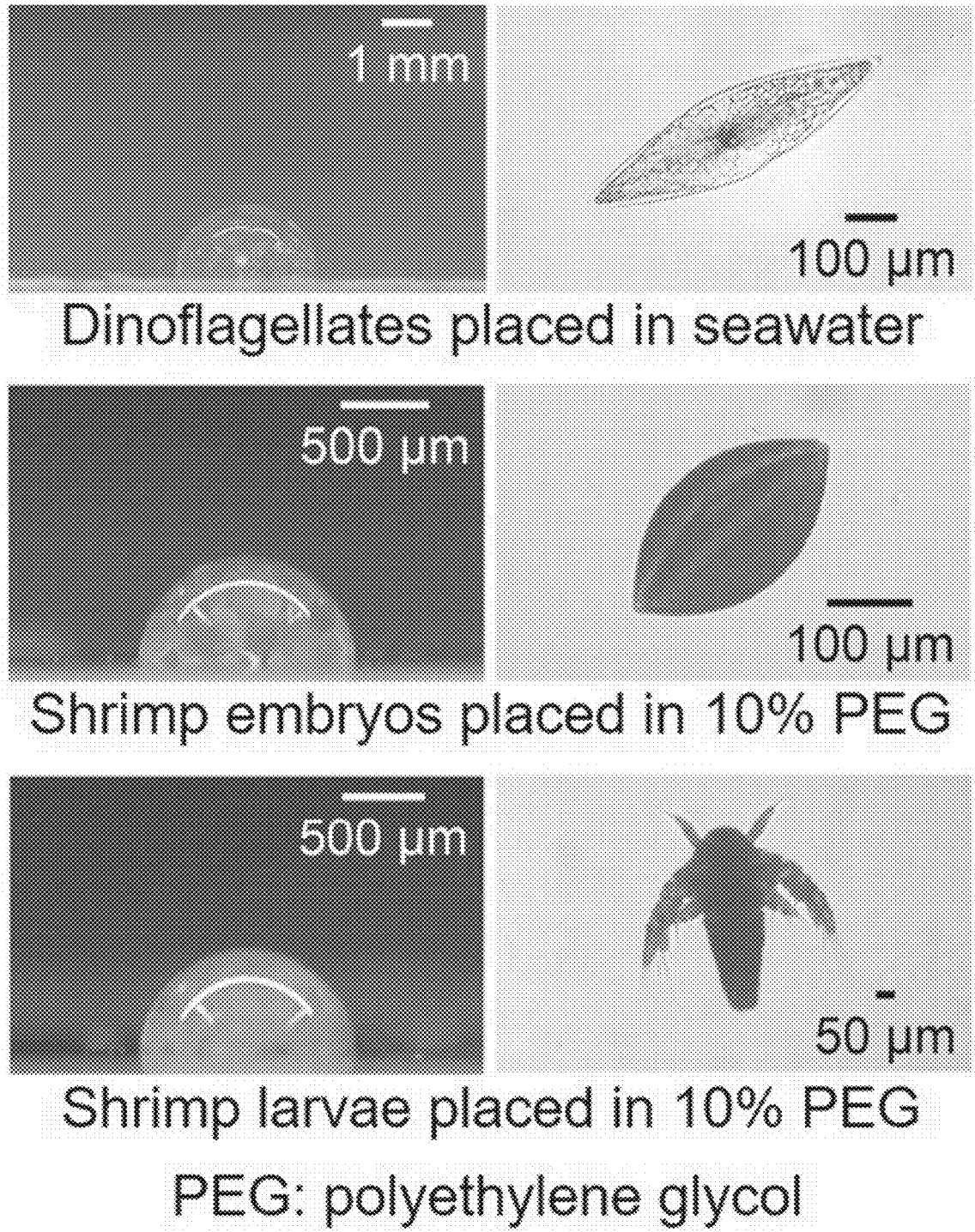

FIG. 19B includes images of example organisms that can be moved using the system 350 of FIG. 16. On the left side of the images are example organisms within a droplet of fluid, and the right side of the images are individual organisms that can be moved or be present within a droplet. The top images include dinoflagellates, the middle images include shrimp embryos, and the bottom images include shrimp larvae.

Example 6

Figure 1:
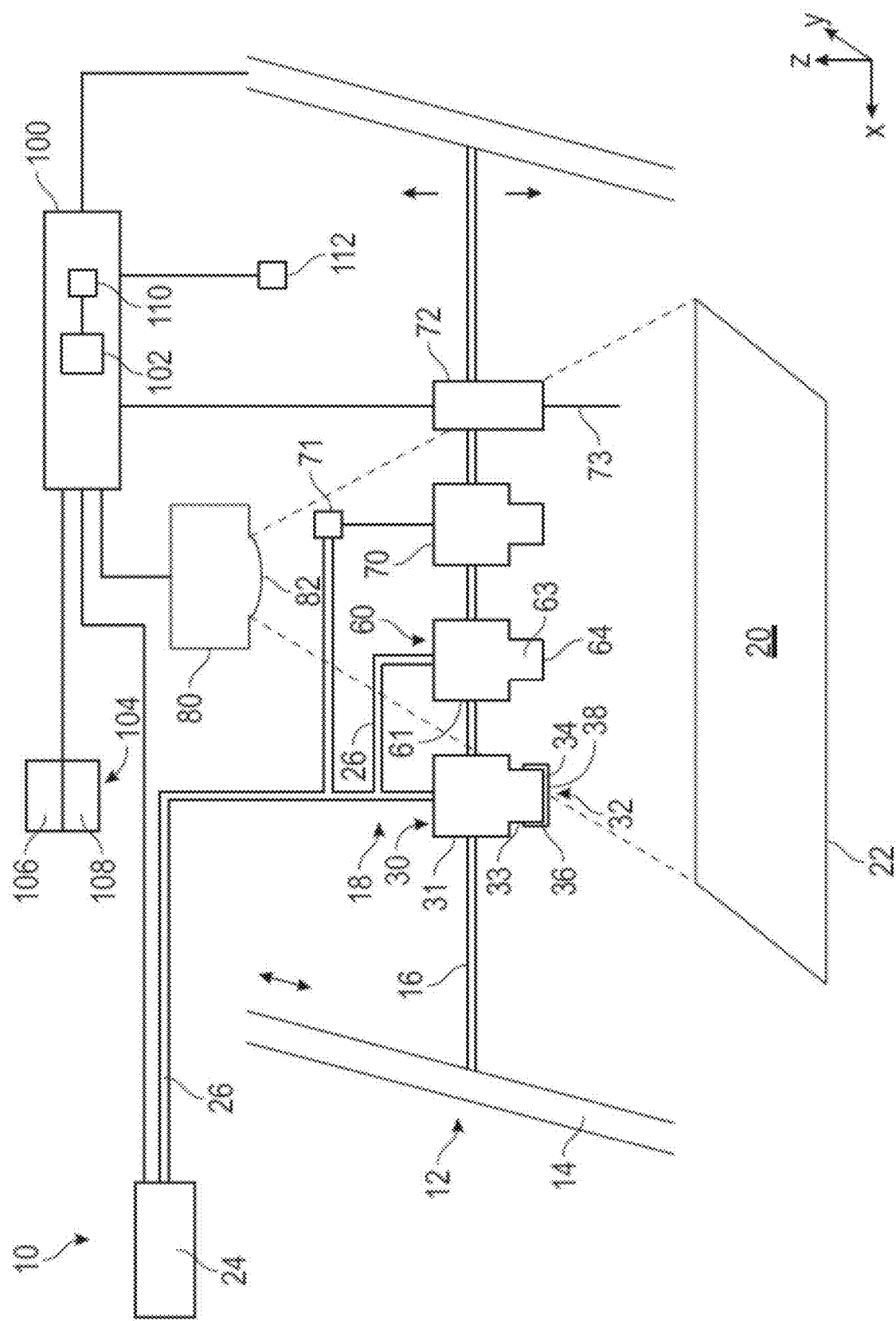
Figure 5:
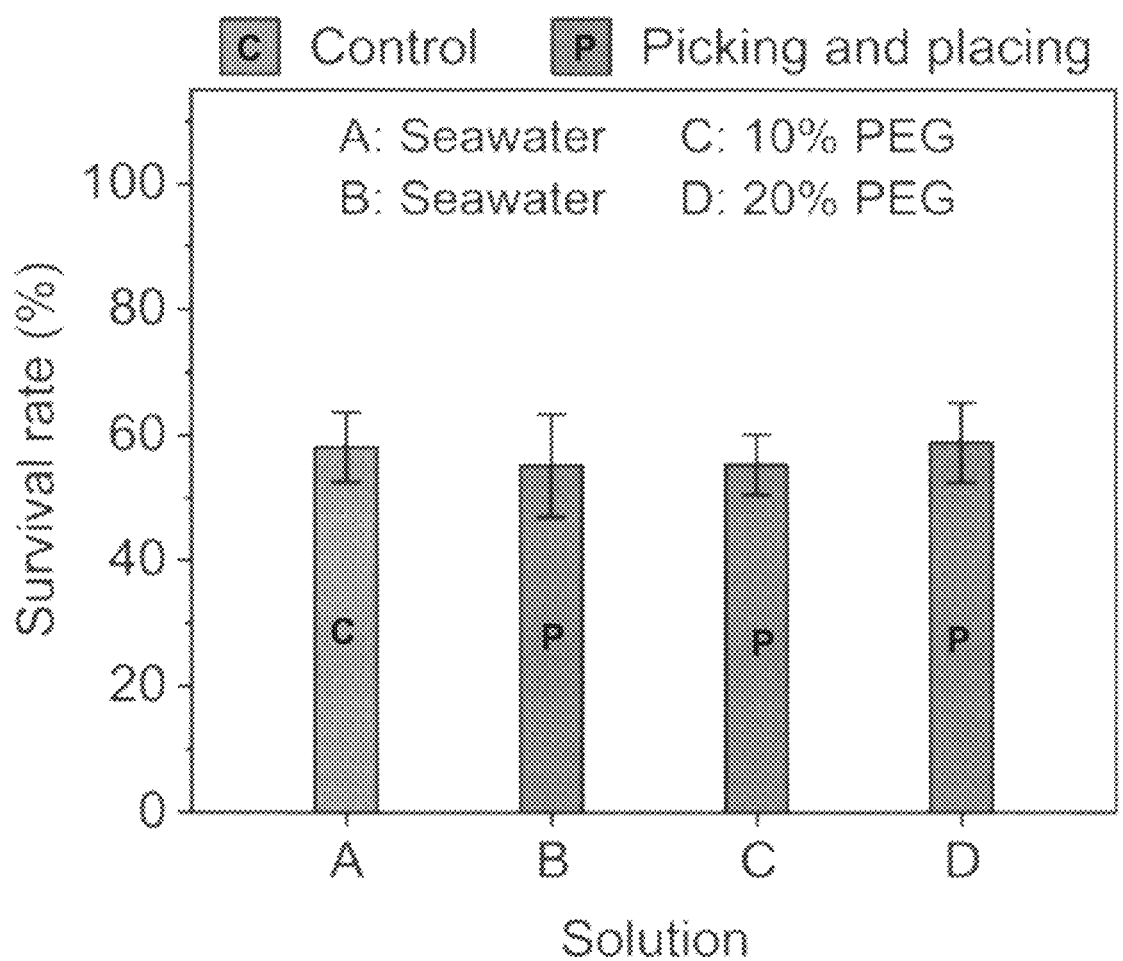
Figure 6A:
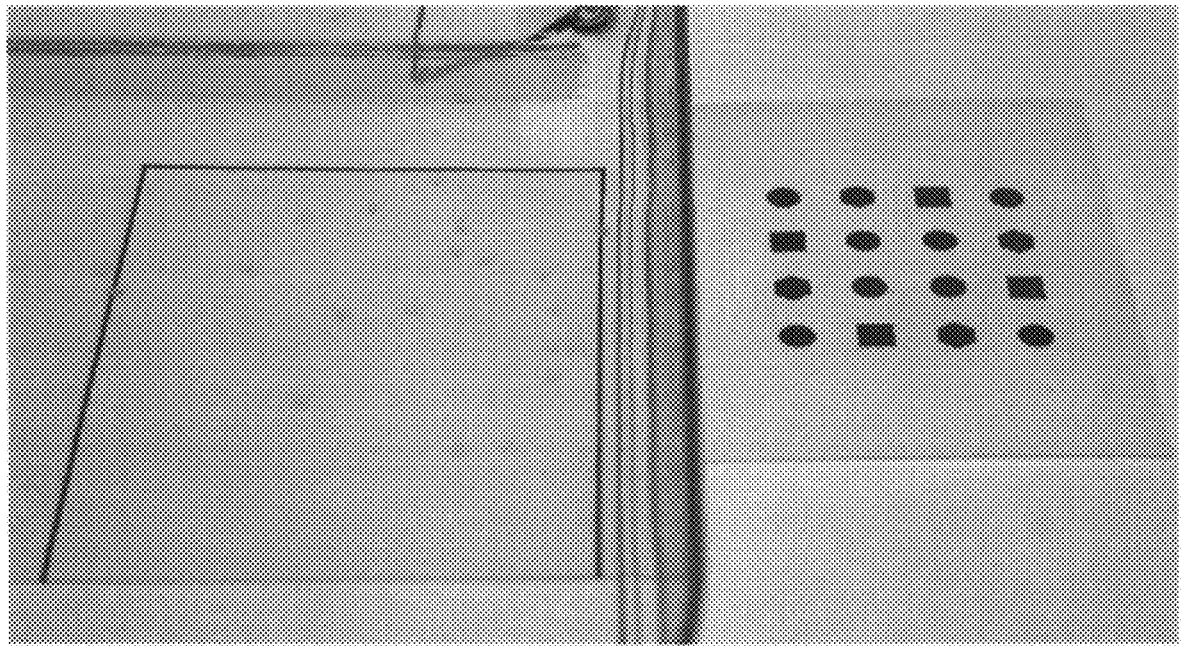
Figure 6B:
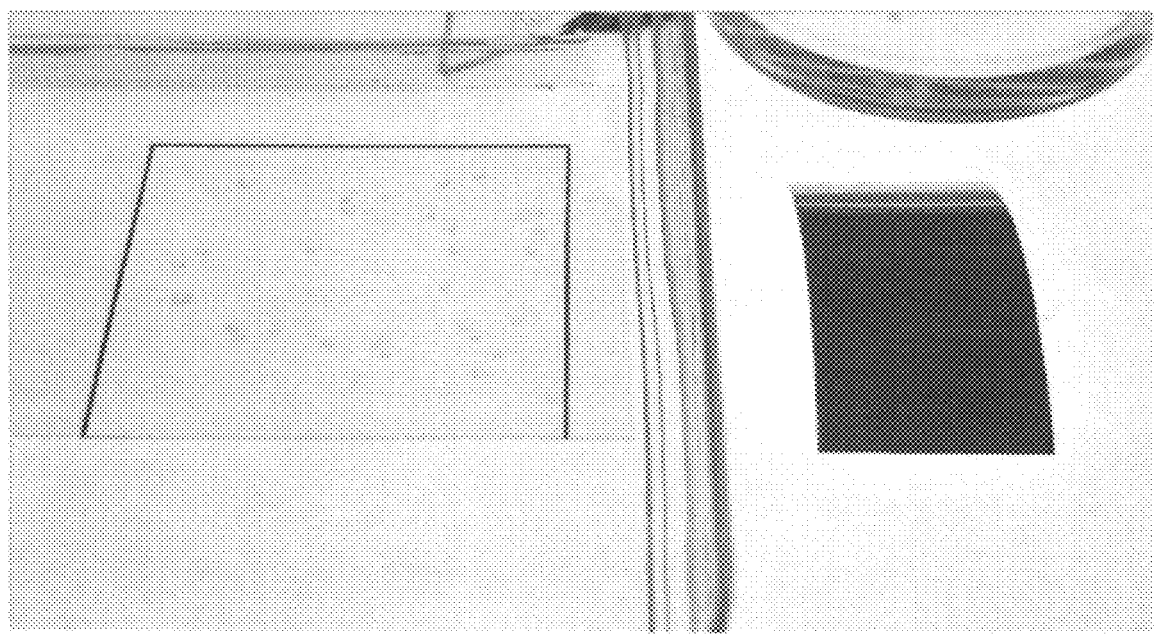
Figure 7:
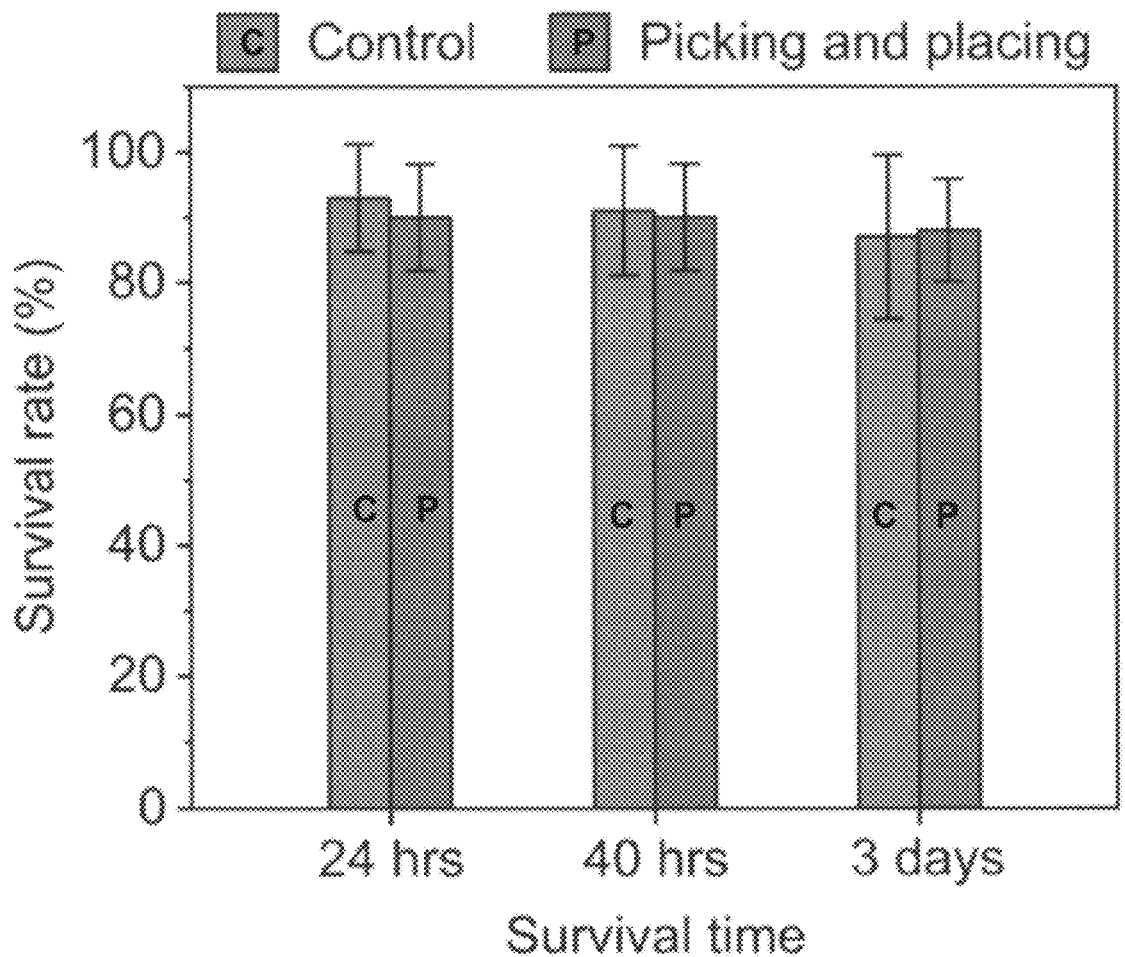
Figure 8:
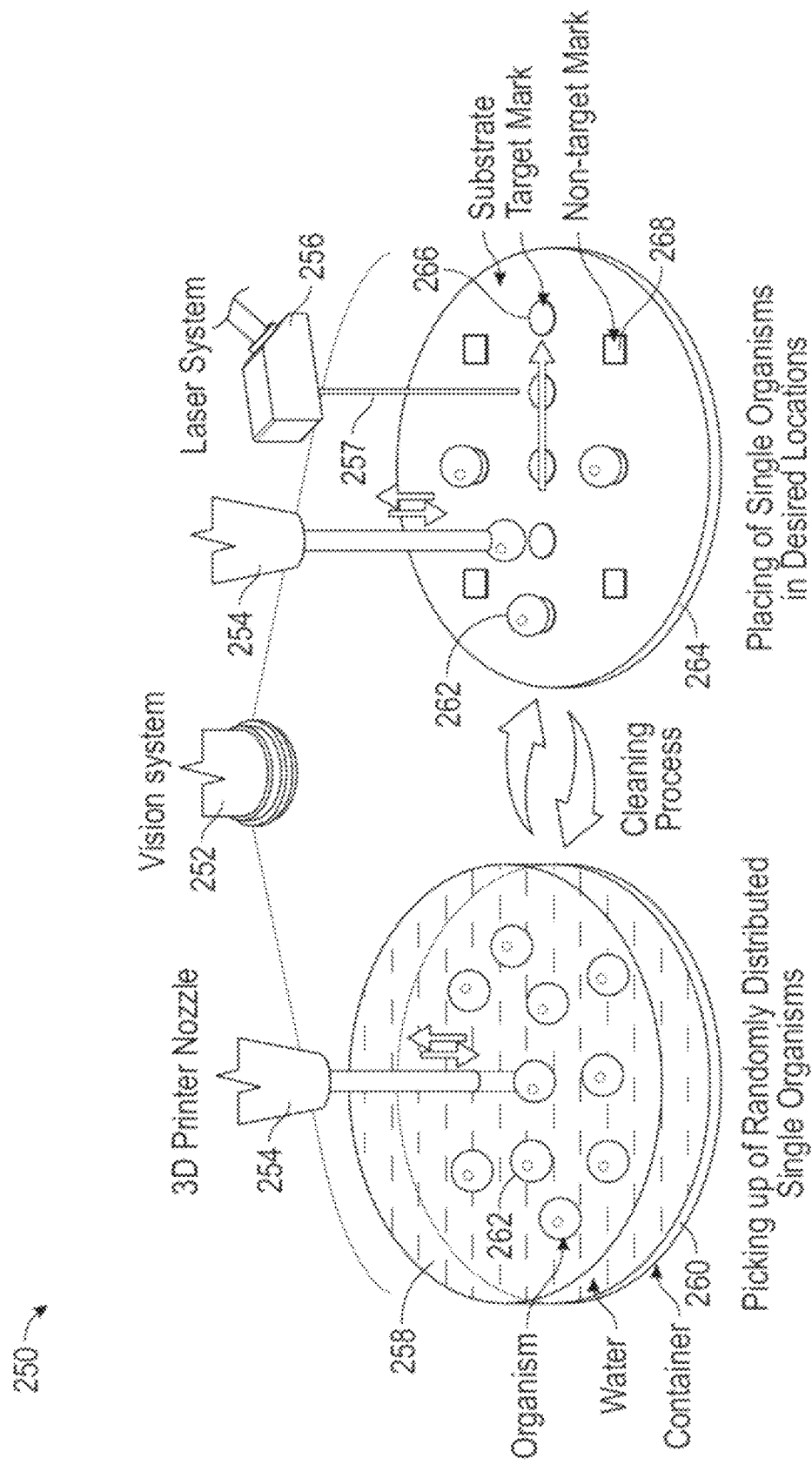
Figure 9:
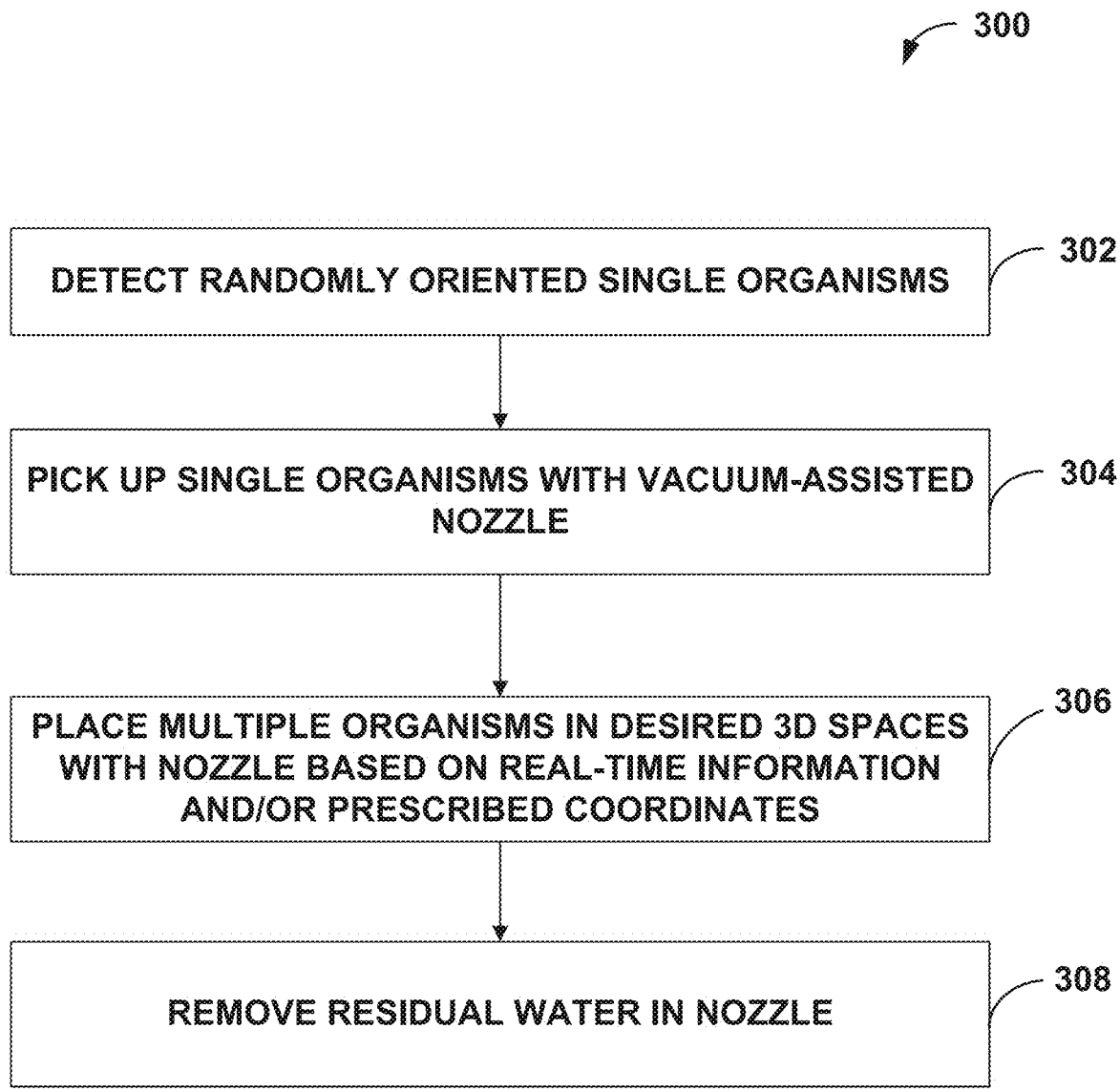
Figure 10:
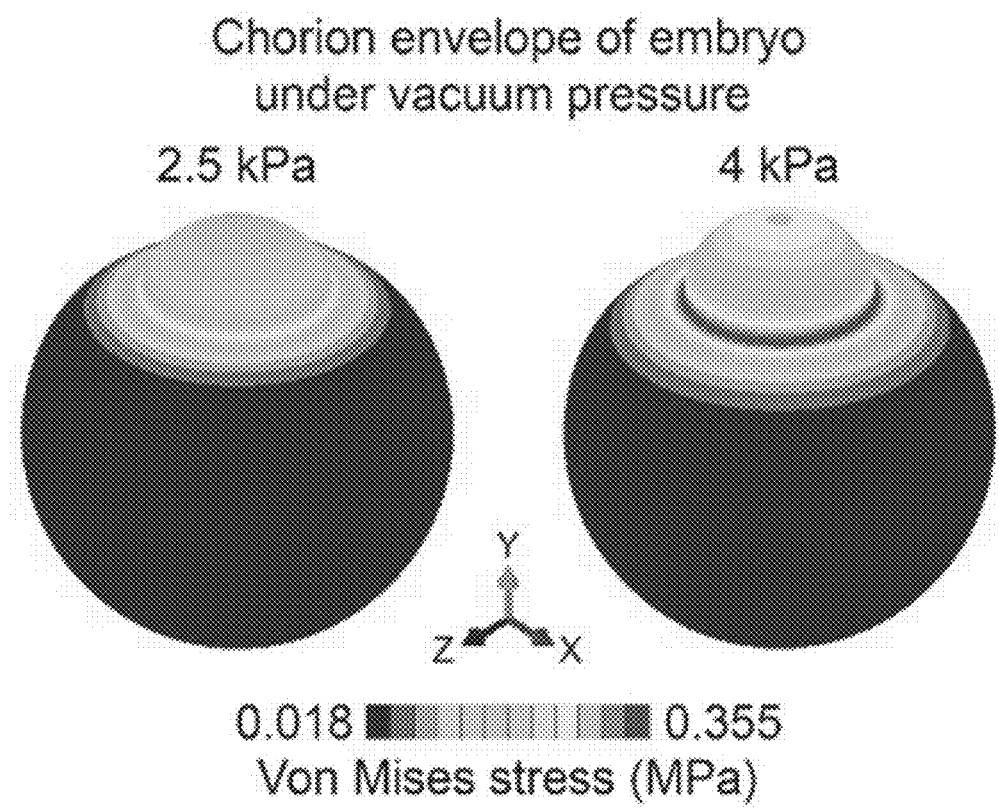
Figure 11:
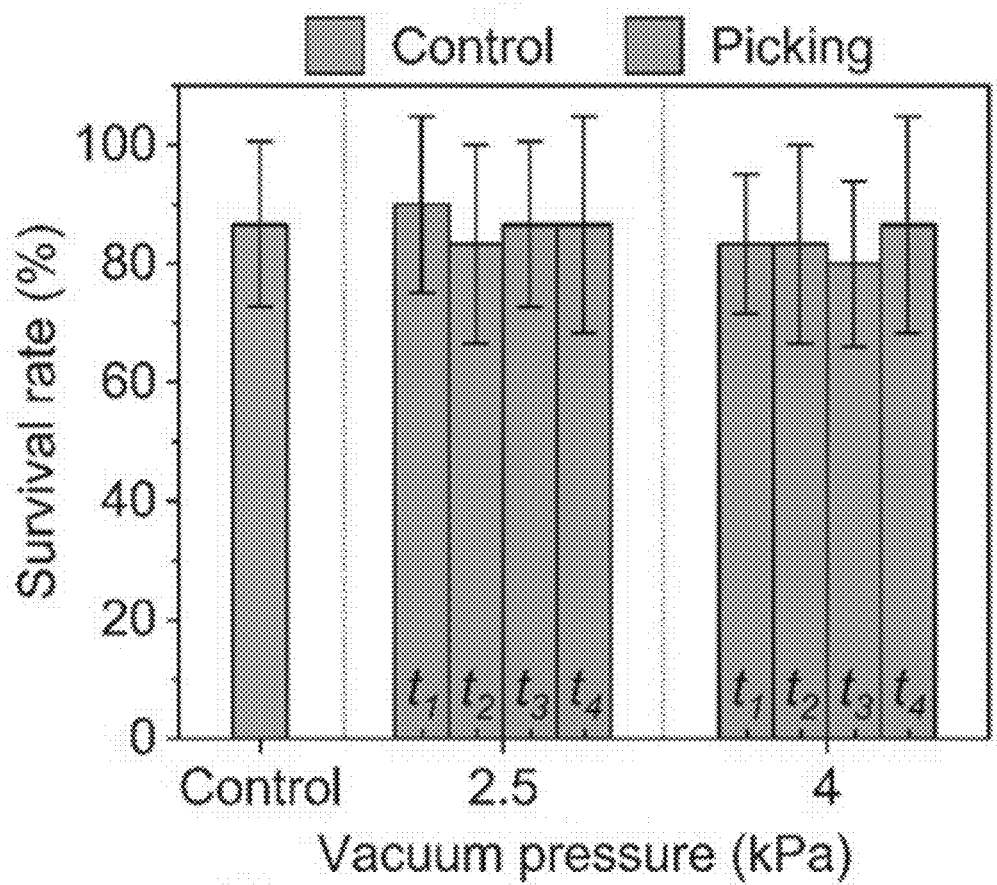
Figure 12:
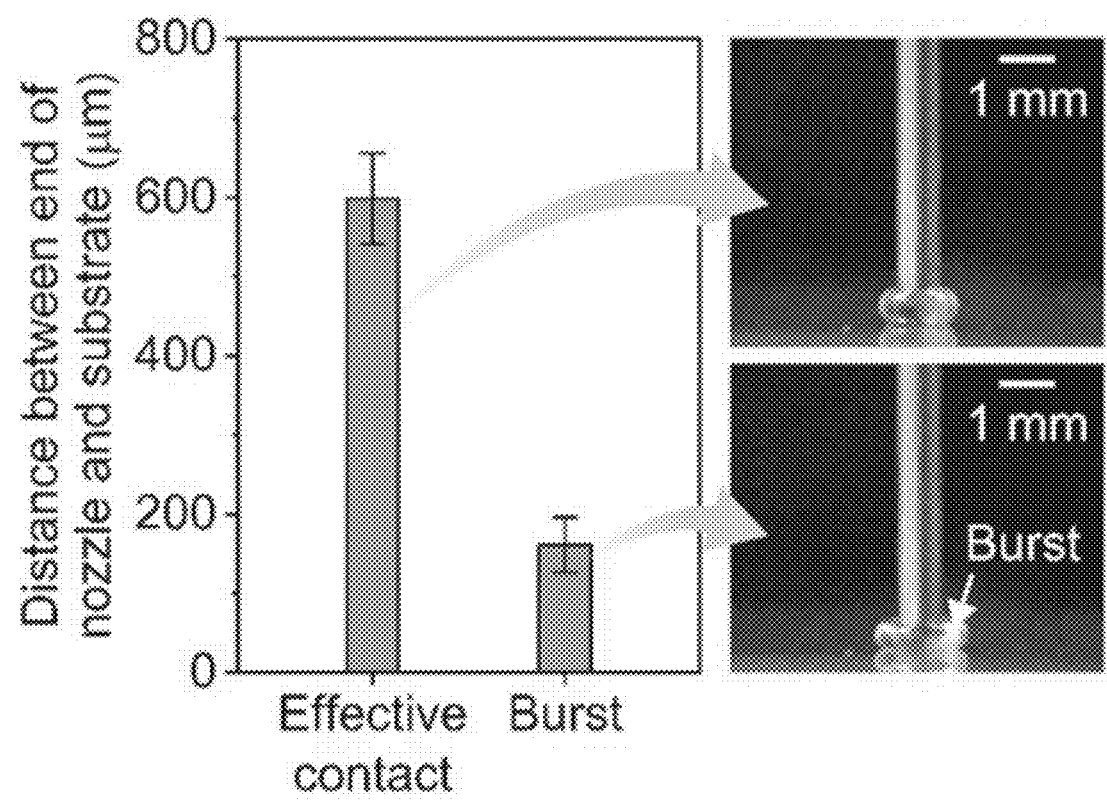
Figure 13:
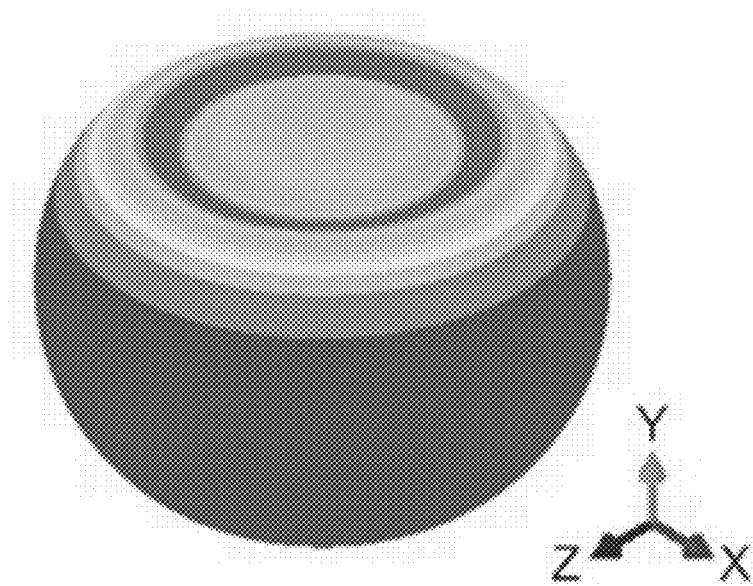
Figure 14:
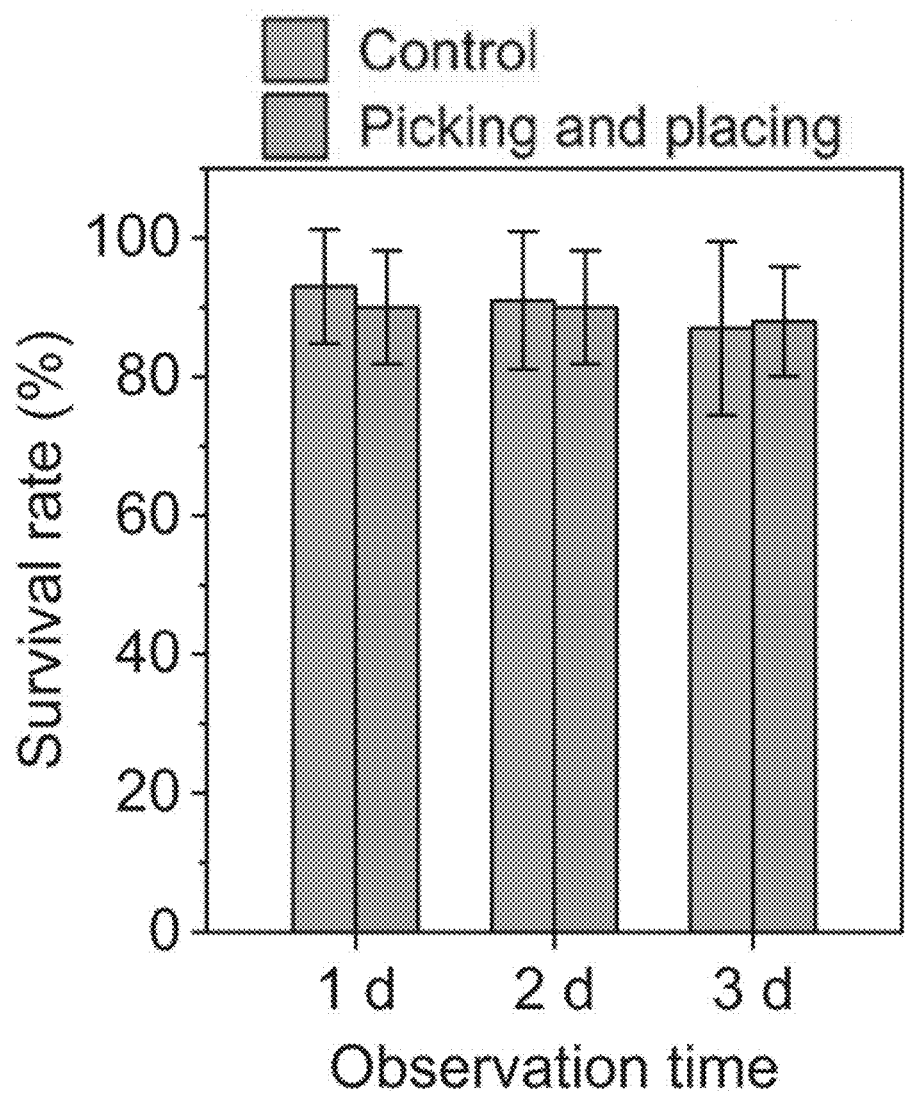
Figure 20:
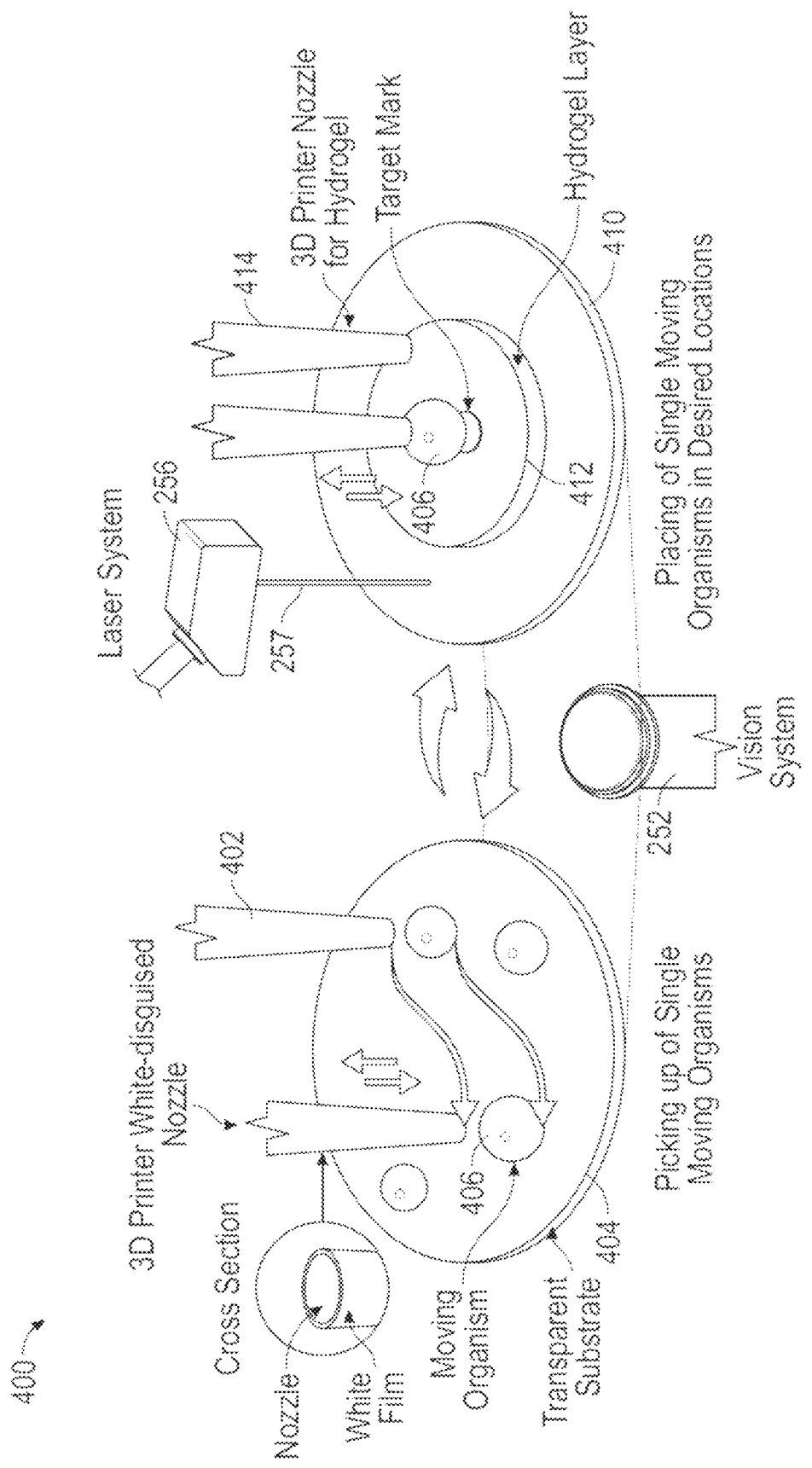

FIG. 20 is a conceptual diagram of an example system 400 for printing single moving organisms. System 400 may be similar to system 10 of FIG. 1, system 250 of FIG. 8, and system 350 of FIG. 16. System 400 includes 3D printer nozzle 402, vision system 252, and laser system 256. 3D printer nozzle 402 may be covered by a film, such as a white film, configured to disguise nozzle 402 from detection by vision system 252. 3D printer nozzle 402 is configured to pick up organisms 406 from substrate 404 which may be transparent in some examples via the location assistance of vision system 252. Using information acquired by vision system 252 and laser system 256, 3D printer nozzle 402 can place organisms 406 on a target mark on the bottom of a hydrogel layer 412 located on substrate 410. In some examples, system 400 also includes 3D printer nozzle 414 configured to dispense the hydrogel for hydrogel layer 412 at the target location on substrate 410. Laser system 256 may be referred to as a distance identification system and can emit a laser beam 257 that is used to determine distances that system 400 uses to control the movement of 3D printer nozzle 402 and/or 3D printer nozzle 414 to the appropriate location on substrate 410 and at the appropriate height. In this manner, system 400 is configured to track and pick up moving organisms and place the organisms at respective desired locations on target substrate 410. Example hydrogels include pluronic hydrogel, and example thicknesses of the hydrogel may be in the range of 0.7 mm to 2.1 mm, or thicknesses lower or higher than these examples.

System 400 can be used with organisms of various elastic moduli and length, such as flexible and small organisms less than (and greater than) 0.5 millimeters in diameter like shrimp larva to more rigid and larger organisms such as beetles with hard exoskeletons. Example organisms include beetles or other insects. 3D printer nozzle 402 may create vacuum pressure that causes the distal end of 3D printer nozzle 402 to retain the target organisms until the vacuum pressure is released. Example vacuum pressure can range from below 2.5 kPa to above 4.0 kPa. Pick up times for system 400 may be less than 0.1 seconds in some examples, but pick up times may be greater than 0.1 seconds in other examples.

Figure 21:
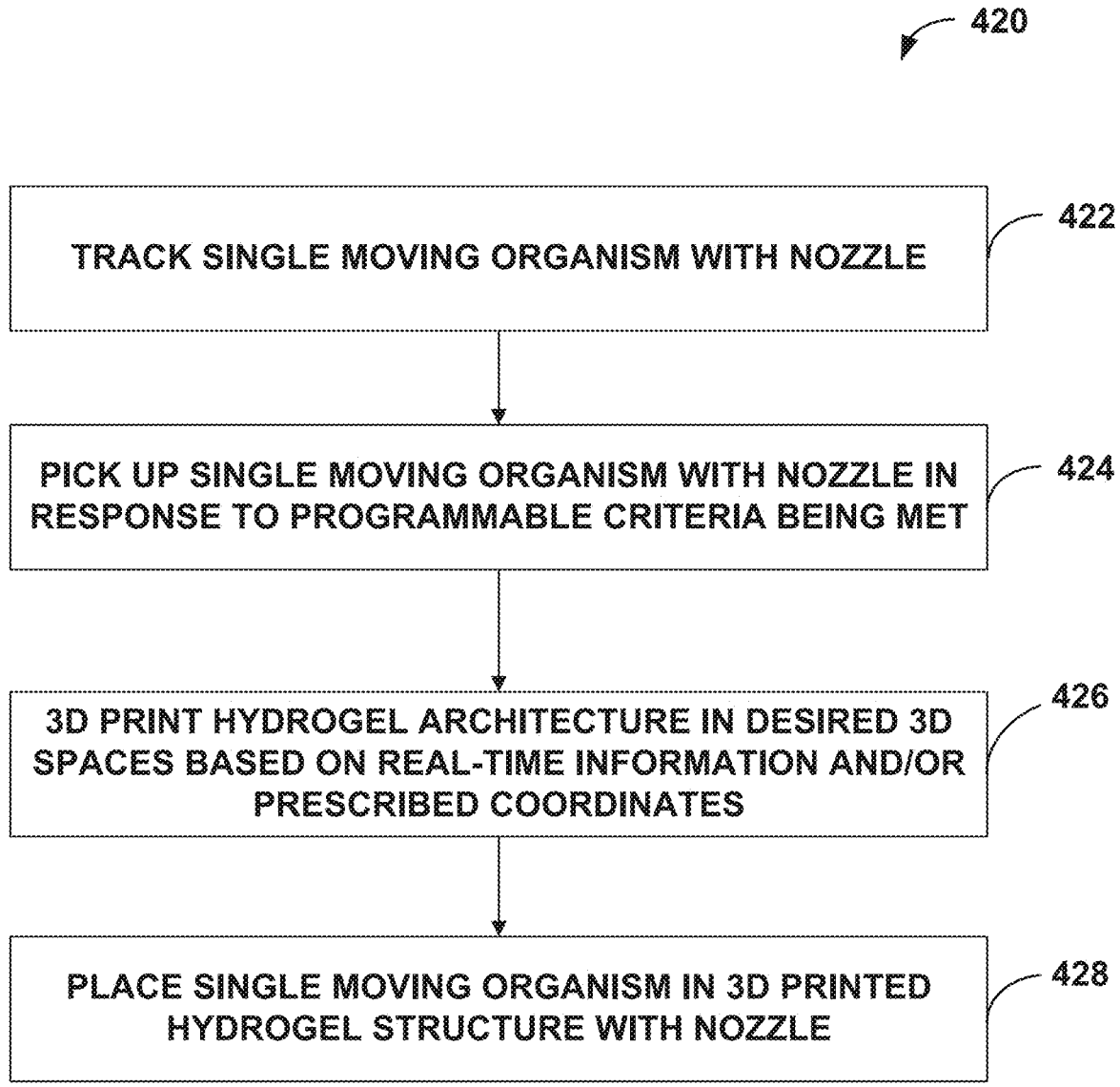

FIG. 21 is a flow chart of an example method of operation of the system of FIG. 20. As shown in technique 420, system 400 can track a single moving organism based on real-time information (e.g., from vision system 252 and the 3D printer) (422). System 400 can then control 3D printing nozzle 402 to pick up the single moving organism with the vacuum assisted nozzle in response to programmable criteria being met, such as preprogramed distance between organisms based on information from vision system 252 and the 3D printer (424). System 400 can then print a hydrogel architecture using nozzle 414 in desired 3D spaces based on real-time information from the vision system 254 and/or laser system 256 and/or prescribed coordinates from the 3D printer controlling 3D printer nozzle 402 (426). Next, system 400 can place the single moving organism in the 3D printed hydrogel structure with nozzle 402 using 3D printer nozzle 402 (428).

Figure 22:
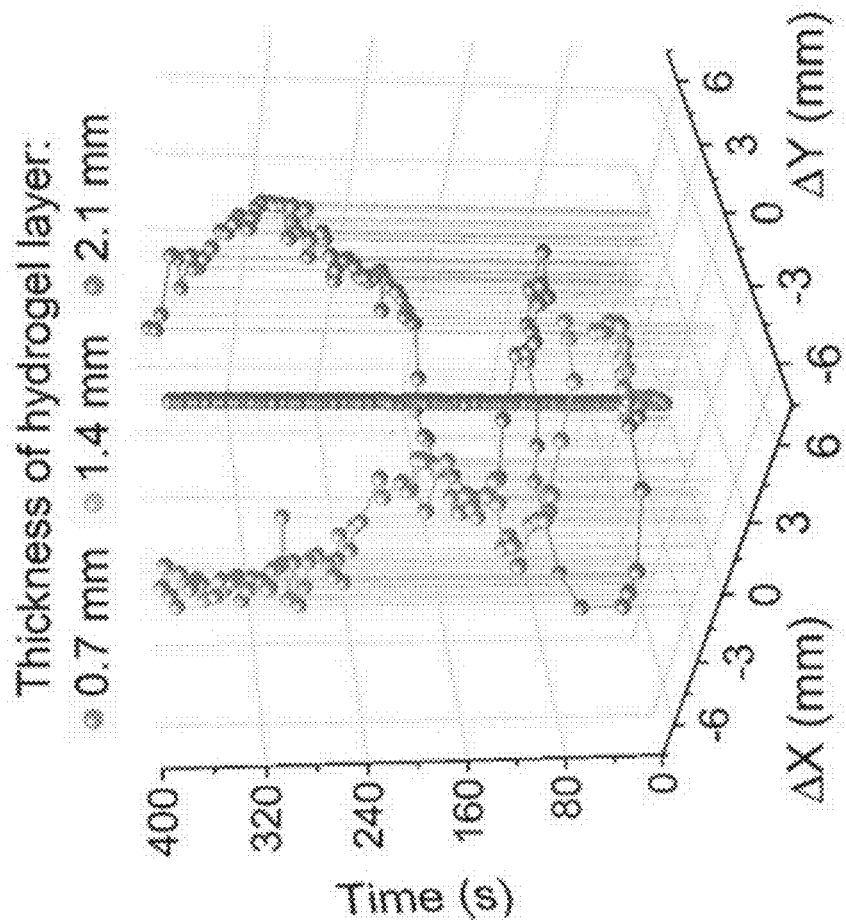

FIG. 22 is a graph of the trajectory of randomly moving beetles in pluronic hydrogel as a function of time and thickness of the hydrogel. In the example thicknesses of 0.7 mm, 1.4 mm, and 2.1 mm, the beetles appear to move similarly in the hydrogel of thicknesses 0.7 mm and 1.4 mm, but did not move in the 2.1 mm thickness hydrogel.

Figure 23A:
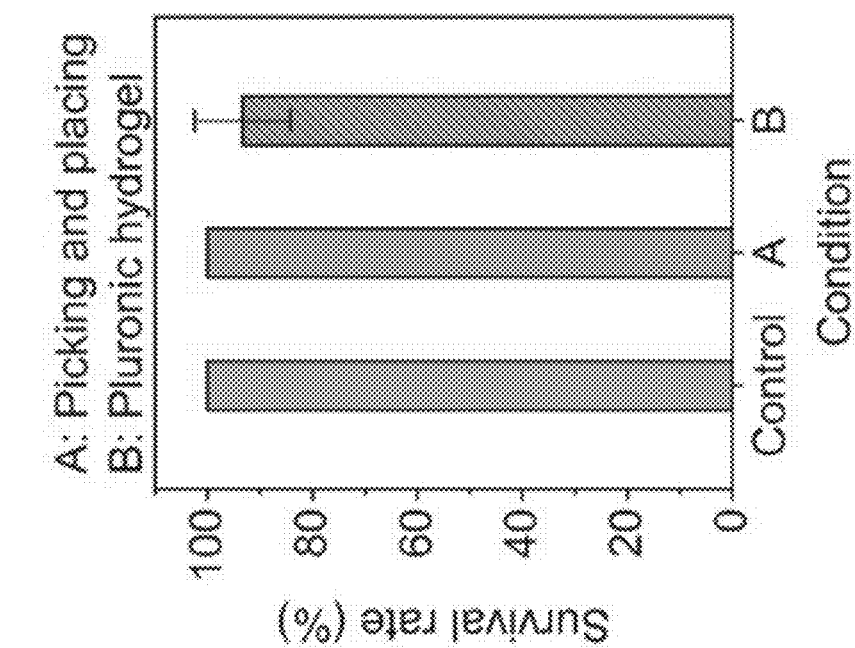

FIG. 23A is a graph of survival rates of example beetles after the picking and placing process where A is the picking and placing process and B is the removal of the hydrogel afterwards. System 400 did not decrease survival rates of organisms consistent with the control group that did not go through any manipulation.

FIG. 23B includes images of example organisms that can be moved using the system of FIG. 20. The top image in FIG. 23B includes images of example beetles that can be placed in pluronic hydrogel using system 400 of FIG. 20. The bottom image of FIG. 23B includes images of beetles that are placed in pluronic hydrogel in the direction of the vision-recognized arrow direction. System 400 may pick up and move these or other organisms that may be moving.

Example 7

Figure 26:
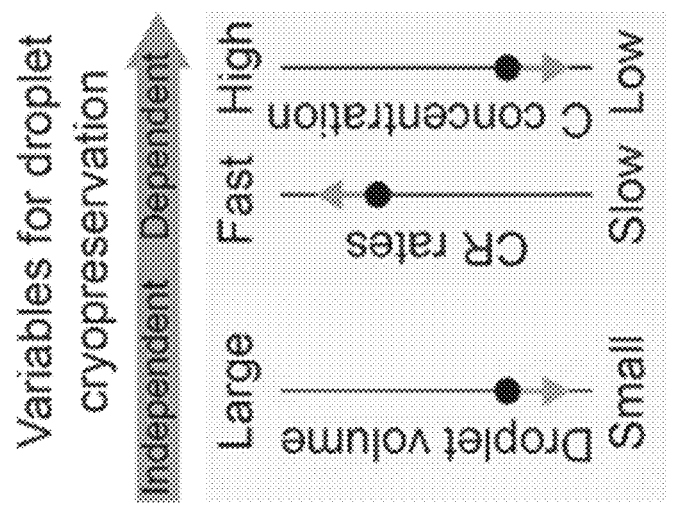
Figure 25:
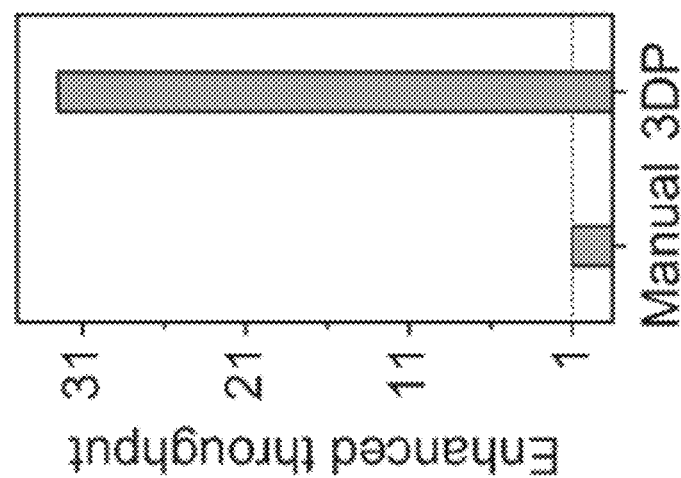
Figure 24:
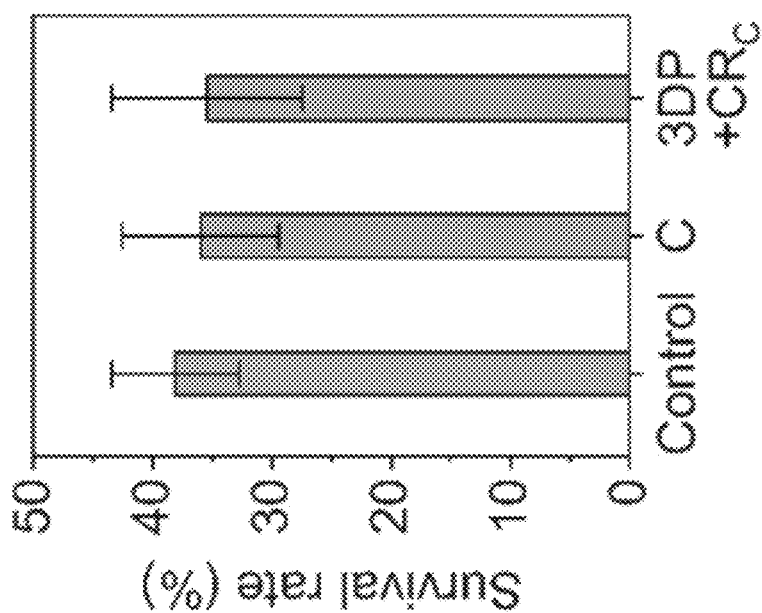

Other types of organisms may be moved using example systems (e.g., system 350) herein, such as zebrafish embryos in cryoprotectant droplets or shrimp embryos in cryoprotectant droplets. FIG. 24 is a graph of survival rates of example cryopreserved shrimp embryos after the printing process. System 350 did not decrease survival rates of organisms consistent with the control group that did not go through any manipulation. FIG. 25 is a graph of the example throughput of manual manipulation versus 3D printing process. FIG. 26 is a graph of the relation between droplet volume and cryopreservation parameters such as cooling and rewarming rates and required cryoprotectant concentration. The system can scale up and down droplet volume, which includes placed organisms. For example, the ability of the system to place organisms in a small droplet volume can enable rapid cooling and rewarming rates and decreased toxicity from low cryoprotectant concentration, which can be advantageous for cryopreservation.

The systems described herein may be used for other purposes or to create different structures. For example, a system may be configured to print dinoflagellates into silicone chambers printed on spherical surface via conformal printing. These silicone chambers may respond to sound and/or respond differently to high and low sound amplitudes. In a planar display example, a system may be configured to provide vision-guided printing of dinoflagellates into silicone chambers printed on planar surface. These structures may also respond to sound. In some examples, the systems may be configured to print structures using functional inks and/or devices onto an organism. For example, the system may be configured to print functional inks and devices on beetles. Some printing may include conformal printing of invisible hydrogel ink with one or more layers onto beetles or other organisms. Functional devices printed onto organisms may include light emitting diodes (LEDs) or LED arrays. The functionality of the 3D printed LED devices can be provided by turning on the LEDs via wireless power transmission of a tesla coil with a ground wire at one side of the device.

The following examples are described herein.

Example 1: A system includes a placement head includes identify at least one target biological organism to be picked up by the at least one printing nozzle of the placement head in a first location; and identify at least one second location for deposit of the at least one target biological organism, wherein the first location is different from the at least one second location; and a robotic motion system configured to move the placement head, based on input from the visual inspection system and a distance identification system, from the first location to the at least one second location, such that the placement head deposits the target biological organism at the at least one second location.

Example 2: The system of example 1, wherein at least a portion of the printing nozzles comprise a screened tip.

Example 3: The system of example 2, wherein the screened tip of the printing nozzle comprises an orifice overlain by a screen with a mesh having an opening size selected to retain a plurality of target biological organisms on an external surface of the screen.

Example 4: The system of example 3, wherein the plurality of target biological organism on the external surface of the screen are entrained in less than about 90% by weight of a liquid medium.

Example 5: The system of any of examples 3 and 4, wherein the opening size in the mesh of the screen is about 1 microns to about 3000 microns.

Example 6: The system of any of examples 3 through 5, wherein the screen has an open area percentage of about 1% to about 99%.

Example 7: The system of any of examples 1 through 6, wherein at least a portion of the printing nozzles comprise an unscreened tip with an orifice having a diameter of about 1 micron to about 3000 microns.

Example 8: The system of example 7, wherein the diameter of the orifice in the unscreened tip is selected to retain an individual target organism by vacuum, adhesives, hydrogels, grippers, hook and loop fasteners, clamps, or soft robotic manipulators such that at least a portion of the individual target organism is external to the tip.

Example 9: The system of example 8, wherein the individual target organism is in a liquid state, a substantially liquid-free state, or in a liquid-free state when retained by the unscreened tip.

Example 10: The system of any of examples 1 through 9, wherein the placement head comprises at least one fluid delivery nozzle.

Example 11: The system of example 10, wherein at least a portion of the fluid delivery nozzles are unscreened.

Example 12: The system of any of examples 1 through 11, wherein the placement head further comprises an illumination source.

Example 13: The system of any of examples 1 through 12, wherein the image acquisition system comprises a visual inspection system configured to identify the target biological organisms.

Example 14: The system of any of examples 12 and 13, wherein the distance identification system captures three-dimensional measurements using the illumination source.

Example 15: The system of any of examples 1 through 14, wherein the robotic motion system is configured to move the placement head in any of the x, y or z directions.

Example 16: The system of any of examples 1 through 15, wherein the second location comprises a drop of a liquid medium.

Example 17: The system of example 16, wherein the drop of the liquid medium has a volume of less than about 1000 microliters.

Example 18: The system of any of examples 16 and 17, wherein the drop of the liquid medium has a volume of less than about 1 microliter.

Example 19: A method for moving at least one target biological organism from a first location to a second location includes identifying with a visual inspection system the at least one target biological organism at the first location to be picked up by a printing nozzle in a placement head, wherein the placement head is moveable in any of an x, y or a z direction with a robotic motion system; applying a vacuum to the printing nozzle to pick up and detachably hold the at least one target biological organism such that at least a portion of the at least one biological organism remains external to the printing nozzle; identifying with a laser distance identification system at least one second location for deposit of the at least one target biological organism, wherein the first location is different from the at least one second location; and moving, with input from the visual inspection system and the distance identification system, the robotic motion system to position the printing nozzle of the placement head at the at least one second location, and applying at least one of a fluid, a gas, or a zero vacuum to the printing nozzle to detach the at least one target biological organism from the printing nozzle and deposit the at least one target biological organism at the at least one second location.

Example 20: The method of example 19, wherein the printing nozzle comprise a screened tip.

Example 21: The method of example 20, wherein the screened tip of the printing nozzle comprises an orifice overlain by a screen with a mesh having an opening size selected to retain a plurality of target biological organisms on an external surface of the screen.

Example 22: The method of example 21, wherein the plurality of target biological organism on the external surface of the screen are entrained in a liquid medium.

Example 23: The method of any of examples 21 and 22, wherein the opening size in the mesh of the screen is about 1 micron to about 3000 microns.

Example 24: The method of any of examples 21 through 23, wherein the screen has an open area percentage of about 1% to about 99%.

Example 25: The method of any of examples 19 through 24, wherein the printing nozzle comprises an unscreened tip with an orifice having a diameter of about 1 micron to about 3000 microns selected to retain an individual target organism such that at least a portion of the individual target organism is external to the tip.

Example 26: The method of example 25, wherein the individual target organism is in a liquid state, a substantially liquid-free state, or in a liquid-free state when retained by the unscreened tip.

Example 27: The method of any of examples 19 through 26, wherein the fluid is a first fluid, wherein the placement head comprises at least one fluid delivery nozzle, and wherein the method further comprises applying, via the at least one fluid delivery nozzle, a second fluid to the at least one target organism at the second location.

Example 28: The method of any of examples 19 through 27, further comprising applying, via a substance nozzle, one or more solid elements with the at least one target biological organism at the at least one second location.

Example 29: The method of example 28, further comprising determining application of the one or more solid elements at the at least one second location via a vision guidance system.

Example 30: The method of any of examples 19 through 29, wherein the placement head further comprises a laser illumination source.

Example 31: The method of example 30, wherein the image acquisition system comprises a visual inspection system configured to identify the target biological organism, and a laser distance identification system configured to capture three-dimensional measurements using the laser illumination source.

Example 32: The method of any of examples 19 through 31, wherein the second location comprises a drop of a liquid medium.

Example 33: The method of example 32, wherein the drop of the liquid medium has a volume of less than about 100 microliters.

Example 34: The method of any of examples 32 and 33, wherein the drop of the liquid medium has a volume of less than about 1 microliter.

Example 35: The method of any of examples 32 through 34, wherein the liquid medium is on a substantially planar surface.

Example 36: The method of any of examples 32 through 35, wherein the liquid medium is on a non-planar surface.

Example 37: The method of any of examples 19 through 36, wherein the second location is occupied by a previously deposited biological organism.

Example 38: The method of example 37, wherein the previously deposited biological organism is on a non-planar surface.

Example 39: The method of any of examples 19 through 38, wherein the at least one target biological organism is alive.

Example 40: The method of any of examples 19 through 39, wherein the image acquisition system is configured to identify live target biological organisms in a mixture of live and dead biological organisms at the first location.

Example 41: The method of any of examples 19 through 40, wherein the first location comprises a reservoir of biological organisms chosen from embryos, larvae, insects, mammals, fish, birds, reptiles, amphibian, trees, herbs, bushes, grasses, vines, ferns, mosses, green algae, and mixtures and combinations thereof.

Example 42: The method of any of examples 19 through 41, wherein the first location comprises a surface with a first coordinate on the z-axis, and the second location has a second coordinate on the z-axis that is different from the first coordinate on the z-axis.

Example 43: The method of any of examples 19 through 42, further comprising cryopreserving the target biological organism at the second location.

Example 44: A printing head for depositing biological organisms, wherein the printing head comprises: at least one meshed printing nozzle comprising an orifice overlain by a screen with a mesh having an opening size selected to retain under a vacuum a plurality of liquid-entrained biological organisms on an external surface of the screen; and at least one meshless printing nozzle comprising an orifice having a diameter of about 1 micron to about 3000 microns selected to retain under a vacuum an individual organism such that at least a portion of the individual organism is external to the tip.

Example 45: The printing head of example 44, wherein the opening size in the mesh of the screen is about 1 micron to about 3000 microns.

Example 46: The printing head of any of examples 44 and 45, wherein the screen has an open area percentage of about 1% to about 99%.

Example 47: The printing head of any of examples 44 through 46, further comprising at least one liquid delivery nozzle.

Example 48: The printing head of any of examples 44 through 47, further comprising an illumination source.

Example 49: The printing head of example 48, wherein the illumination source comprises a laser distance identification system.

Example 50: A method for assembling organisms includes identifying with a visual inspection system the at least one target biological organism at a first location to be picked up by a nozzle in a printing head, wherein the printing head is moveable in any of an x, y or a z direction with a robotic motion system; applying a vacuum to the nozzle to pick up and detachably hold the at least one target biological organism such that at least a portion of the at least one biological organism remains external to the nozzle; identifying with a distance identification system at least one second location for deposit of the at least one target biological organism, wherein the first location is different from the at least one second location, and wherein a biological structure resides in the at least one second location; and moving, with input from the visual inspection system and the distance identification system, the robotic motion system to position the nozzle of the printing head at the at least one second location, and applying a fluid to the nozzle to detach the at least one target biological organism from the printing nozzle and deposit the at least one target biological organism on the biological structure at the at least one second location.

Various embodiments of the disclosure have been described. These and other embodiments are within the scope of the following claims.

What is claimed is:

1. A system comprising:
a vacuum line;
a vacuum system configured to create a vacuum in the vacuum line;
a placement head comprising at least one printing nozzle fluidly connected to the vacuum line and configured to apply the vacuum to at least one target biological organism to pick up and detachably hold the at least one target biological organism at one or more openings of the at least one printing nozzle, wherein the at least one printing nozzle defines the one or more openings that are each smaller than a cross-sectional area of each target biological organism of the at least one target biological organism, and wherein each opening of the one or more openings have a diameter from 1 micron to 3,000 microns;
at least one camera;
a laser illumination source;
a visual inspection processing system configured to:
 receive, from the at least one camera, a plurality of images of at least one surface at which the at least one target biological organism is disposed;
 identify, from at least one image of the plurality of images, the at least one target biological organism to be picked up by the at least one printing nozzle of the placement head in a first location; and
 identify, from at least one image of the plurality of images, at least one second location for deposit of the at least one target biological organism, wherein the first location is different from the at least one second location; and
a distance identification processing system configured to determine, using light from the laser illumination source, one or more distances to the at least one surface;
a robotic motion system coupled to the placement head; and
a controller comprising processing circuitry configured to:
 control application of the vacuum to the at least one printing nozzle to pick up the at least one target biological organism at the first location;
 control, based on at least one image of the plurality of images and the one or more distances, the robotic motion system to move the placement head from the first location to the at least one second location; and
 control the application of the vacuum and the placement head to deposit the at least one target biological organism at the at least one second location.

2. The system of claim 1, wherein at least a portion of the at least one printing nozzle comprises a screened tip, the screened tip defining a plurality of openings comprising the one or more openings.

3. The system of claim 2, wherein the one or more openings comprises a plurality of openings and wherein the at least one target biological organisms comprises a plurality of biological organisms, and wherein the screened tip of the at least one printing nozzle comprises an orifice overlain by a screen with a mesh defining an opening size of each opening of the plurality of openings that is smaller than the cross-sectional area than each target biological organism of the plurality of target biological organisms, and wherein the controller is configured to control the application of the vacuum to the printing nozzle to retain a plurality of target biological organisms on an external surface of the screened tip under suction caused by the vacuum.

4. The system of claim 3, wherein the controller is configured to control the application of the vacuum to the printing nozzle to pick and hold the plurality of target biological organisms on the external surface of the screen from a liquid medium in which the plurality of target biological organisms are entrained in less than about 90% by weight of the liquid medium.

5. The system of claim 3, wherein the opening size in the mesh of the screen is about 1 microns to about 3000 microns.

6. The system of claim 3, wherein the screen is formed from one of a metal, a polymeric material, a ceramic material, a hydrogel material, or a biological material.

7. The system of claim 1, wherein the one or more openings comprises a single orifice, and wherein at least a portion of the at least one printing nozzle comprises an unscreened tip with the single orifice having the diameter of about 1 micron to about 3000 microns.

8. The system of claim 7, wherein the diameter of the single orifice in the unscreened tip is configured to be smaller than a cross-sectional area of one target biological organism of the at least one target biological organisms, and wherein the controller is configured to control the application of the vacuum to the printing nozzle to retain at least a portion of the one target biological organism external to the unscreened tip.

9. The system of claim 1, wherein the placement head comprises at least one fluid delivery nozzle configured to deliver fluid, the fluid delivery nozzle being different from the at least one printing nozzle.

10. The system of claim 9, wherein at least a portion of the at least one fluid delivery nozzle is unscreened.

11. The system of claim 1, wherein the placement head further comprises the laser illumination source.

12. The system of claim 11, wherein the distance identification processing system is configured to determine, based on the light from the laser illumination source and at least one image of the plurality of images, three-dimensional measurements between the placement head, the at least one target biological organism, and the at least one surface.

13. The system of claim 1, wherein the controller is configured to control the robotic motion system to move the placement head in three dimensions with respect to the at least one surface.

14. The system of claim 1, wherein the visual identification processing system is configured to identify, from the at least one image of the plurality of images, a drop of a liquid medium at the at least one second location to deposit the at least one target biological organism.

15. The system of claim 14, wherein the controller is configured to control the application of the vacuum and the placement head to place the at least one target biological organism in the drop of the liquid medium having a volume of less than about 1000 microliters.

16. The system of claim 14, wherein the controller is configured to control the application of the vacuum and the placement head to place the at least one target biological organism in the drop of the liquid medium having a volume of less than about 1 microliter.

17. The system of claim 1, wherein the controller is configured to:
track, based on the plurality of images, movement of the at least one target biological organism with respect to the at least one surface in real-time;
control, according to the tracked movement, the robotic motion system to move the placement head to the at least one target biological organism; and control the placement head to pick up, using the at least one printing nozzle, the at least one target biological organism that is moving with respect to the at least one surface.

18. The system of claim 1, wherein the robotic motion system comprises parallel tracks and a crossmember configured to traverse the parallel tracks, wherein the placement head is attached to the crossmember.

* * * * *